| United States Patent [19] | [11] Patent Number: 4,694,013 |
| Lahm | [45] Date of Patent: Sep. 15, 1987 |

[54] INSECTICIDAL AND ACARICIDAL PHENOXYPYRDINYL ESTERS AND INTERMEDIATES

[75] Inventor: George P. Lahm, Hockessin, Del.

[73] Assignee: E. I. Du Pont de Nemours and Company, Wilmington, Del.

[21] Appl. No.: 910,942

[22] Filed: Sep. 26, 1986

Related U.S. Application Data

[63] Continuation-in-part of Ser. No. 796,152, Nov. 8, 1985, abandoned.

[51] Int. Cl.$^4$ .................. A61K 31/44; C07D 213/61; C07D 213/62
[52] U.S. Cl. ......................... 514/345; 514/338; 514/; 514/350; 546/270; 546/300; 546/301; 546/302; 546/298
[58] Field of Search ............... 546/300, 301, 302, 298, 546/270; 514/338, 345, 350

[56] References Cited

U.S. PATENT DOCUMENTS

| 4,162,366 | 7/1979 | Engel | 568/637 |
| 4,163,787 | 8/1979 | Malhotra et al. | 424/263 |
| 4,221,799 | 9/1980 | Van Heertum et al. | 424/263 |
| 4,323,574 | 4/1982 | Henrick | 424/263 |
| 4,332,815 | 6/1982 | Engel | 424/274 |

FOREIGN PATENT DOCUMENTS

| 0034055 | 10/1983 | Australia | 424/263 |
| 0061114 | 3/1982 | European Pat. Off. | 424/263 |
| 0145661 | 11/1984 | European Pat. Off. | 424/263 |
| 2810881 | 9/1978 | Fed. Rep. of Germany | 424/263 |
| 2108123 | 10/1982 | United Kingdom | 424/263 |

OTHER PUBLICATIONS

Recent Advances in the Chem. of Insect Control, Jones, Royal Soc. of Chem., Burlington House, 1985, p. 153.

*Primary Examiner*—Henry R. Jiles
*Assistant Examiner*—J. Richter
*Attorney, Agent, or Firm*—James A. Costello

[57] ABSTRACT

Insecticidal and acaricidal organic esters formed from pyrethroid carboxylic acids and phenoxypyridinyltrifluoroethanols, agricultural compositions containing said esters and their use against anthropod pests including soil-dwelling species; also, intermediates for these insecticides and acaricides and a process for the preparation of said intermediates.

53 Claims, No Drawings

INSECTICIDAL AND ACARICIDAL PHENOXYPYRDINYL ESTERS AND INTERMEDIATES

CROSS REFERENCE TO RELATED APPLICATION

This application is a continuation-in-part of copending application bearing U.S. Ser. No. 796,152 filed on Nov. 8, 1985, now abandoned.

BACKGROUND OF THE INVENTION

This invention concerns phenoxypyridinyl ester insecticides and acaricides, intermediates for their preparation, agricultural compositions containing the insecticides and acaricides and their use to control pests.

U.S. Pat. No. 4,162,366 discloses the following alcohol for use in the preparation of insecticidal esters:

DE No. 2,810,881 discloses compounds of the following formula as insecticides:

wherein
X is independently $C_1$ to $C_4$ alkyl, $C_1$ to $C_4$ alkoxy, $C_1$ to $C_4$ alkylthio, $C_1$ to $C_4$ alkylsulfonyl, $CF_3$, 3,4-methylenedioxy, Cl, F, or Br;
n is 0, 1 or 2;
Y is O or S;
R is H, CN, or C≡CH; and
Z is Cl, F or Br.

EP No. 145,661 discloses the following intermediates in the synthesis of insecticides:

wherein
X and Y are H, halo, $NO_2$, $C_1$ to $C_4$ alkyl, $C_1$ to $C_4$ haloalkyl, $C_1$ to $C_4$ alkoxy, $C_2$ to $C_5$ alkenyl, or $C_2$ to $C_5$ alkynyl.

AU No. 84/34,055 discloses compounds of the following formula as insecticides:

wherein
W is halogen;
X is H, CN, or C≡CH;
Y is H, $C_1$ to $C_4$ alkyl, $C_1$ to $C_4$ alkoxy, $C_1$ to $C_4$ alkylthio, $C_1$ to $C_4$ alkylsulfonyl, $CF_3$, 3,4-methylenedioxy, Cl, F or Br;
n is 1 or 2; and
Z is H, Cl or F.

U.S. Pat. No. 4,221,799 discloses compounds of the following formula as insecticides:

wherein
n is 0, 1, or 2;
X is independently $C_1$ to $C_4$ alkyl, $C_1$ to $C_4$ alkoxy, $C_1$ to $C_4$ alkylthio, $C_1$ to $C_4$ alkylsulfinyl, $C_1$ to $C_4$ alkylsulfonyl, $CF_3$, $NO_2$, CN, Cl, F, Br, or 3,4-methylenedioxy; and
R is H, CN, or C≡CH.

U.S. Pat. No. 4,332,815 discloses compounds of the following formula as insecticides:

wherein
one of Y and Z is $C_1$ to $C_4$ perhaloalkyl and the other is H, halo, lower alkyl, phenyl, phenylthio, or benzyl;
provided that Y and Z may be combined to form a perhalocyclopentylidene group;
R is allethrolonyl, tetrahydrophthalimidomethyl, or $R^1$;
provided that $R^1$ is other than phenoxybenzyl, α-cyanophenoxybenzyl, or α-ethylnylphenoxybenzyl;
$R^2$ is H, lower alkyl, ethynyl, CN, or trihalomethyl;
$R^3$ is divalent O, divalent S, or vinylene; and
$R^4$, $R^5$, and $R^6$ are independently H, lower alkyl, halogen, lower alkenyl, phenyl, phenoxy, benzyl, phenylthio, or any two joined to form a divalent methylenedioxy group;
provided that when $R^4$, $R^5$ and $R^6$ contains a phenyl ring, it may be substituted with one to three substituents selected from halogen or lower alkyl.

European Patent Application No. 61,114 discloses esters of the following formula to be useful as insecticides:

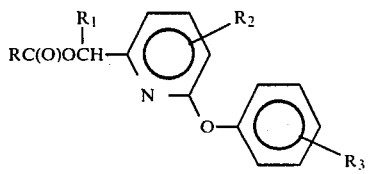

wherein:
R is

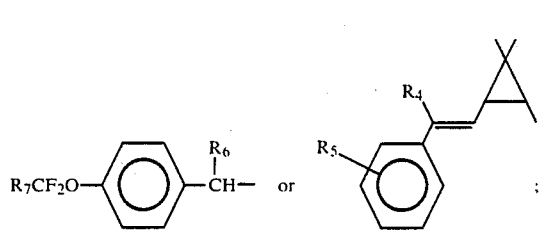

R₁ is H, CN or optionally halo substituted C₁–C₄ alkyl, alkenyl or alkynyl;
R₂ is H or halogen;
R₃ is H or halogen;
R₄ is H, Cl, Br, CN or optionally halo substituted alkyl;
R₅ is H, halogen or optionally halo substituted alkyl or alkoxy;
R₆ is isopropyl or cyclopropyl; and
R₇ is H, F, CF₃, CHFCl or CF₂Cl.

G.B. No. 2,108,123 discloses esters of the following formula to be useful as insecticides:

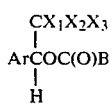

wherein:
Ar represents an optionally substituted aromatic or heteroaromatic radical;
X₁, X₂, and X₃, which may be the same or different each represent a hydrogen atom or a halogen atom, with the proviso that at least one represents a halogen atom; and B represents an alkyl radical of from 1 to 18 carbon atoms or a radical of the formula

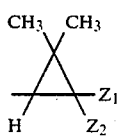

with the exception of compounds of the general formula in which X₁, X₂ and X₃ each represents a fluorine.

*Recent Advances In The Chemistry Of Insect Control*, Janes (ed.), Royal Society of Chemistry, Burlington House, 1985, page 153, discloses a table of phenoxypyridyl esters of the formula:

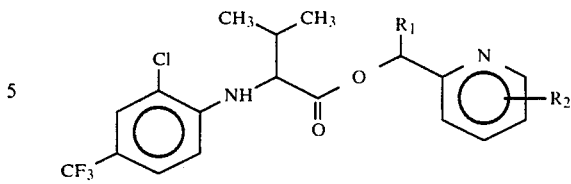

wherein:
R₁ is H, CN, CH₃, CH₂CH₃, ethynyl, ethenyl, CF₃ or CH₃CO₂ and R₂ is phenyl or phenoxy.

U.S. Pat. No. 4,323,574 discloses compounds of the following formula as insecticides

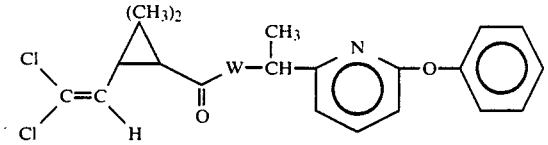

wherein:
W is O or S.

SUMMARY OF THE INVENTION

This invention concerns phenoxypyridinyl ester compounds of Formula I, suitable agricultural compositions containing them, and use of said compounds as insecticides. Compounds of Formula I are characterized by a 1,3 relationship between the ester (RCO₂CHCF₃—) and ether (-x-optionally substituted phenyl) substituents on the pyridine ring. This invention includes all geometric and stereoisomer forms of such compounds of Formula I. This invention also concerns particular alcohol and ketone intermediates employed to make the compounds of Formula I and processes for making said intermediates. The intermediates are likewise characterized by a 1,3 relationship between the alcohol/ketone and ether substituents on the pyridine ring.

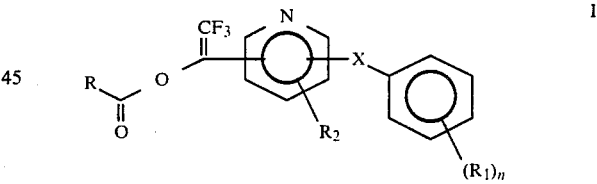

wherein:
R is

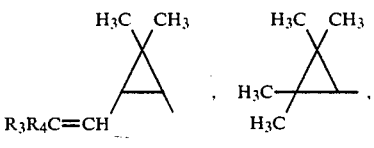

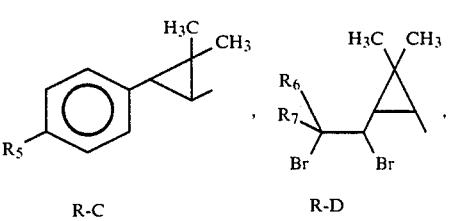

-continued

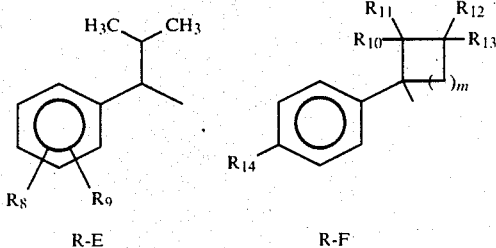

R-E  R-F

X is O or S;
n is 1 to 3;
m is 0 or 1;
$R_1$ is H, $C_1$ to $C_4$ alkyl, $C_2$ to $C_5$ alkenyl, $C_2$ to $C_5$ alkynyl, $C_1$ to $C_4$ haloalkyl, $C_1$ to $C_4$ alkoxy, $C_1$ to $C_4$ haloalkoxy, $C_1$ to $C_4$ alkylthio, $C_1$ to $C_4$ alkylsulfinyl, $C_1$ to $C_4$ alkylsulfonyl, $C_1$ to $C_4$ haloalkylthio, $C_1$ to $C_4$ haloalkylsulfonyl, F, Cl, Br; when n=2, the $R_1$ substituents, taken together, can be 3,4-methylenedioxy;
$R_2$ is H, F, Cl, Br, $CH_3$, or $CF_3$;
$R_3$ is F, Cl, Br, $C_1$ to $C_4$ alkyl, $C_1$ to $C_4$ haloalkyl, $CO_2CH_3$, or $CO_2CH_2CH_3$;
$R_4$ is F, Cl, Br, or $CH_3$;
$R_5$ is H, F, Cl, $CF_3$, or $C_1$ to $C_4$ alkyl;
$R_6$ is Cl or Br;
$R_7$ is Cl or Br;
$R_8$ is H, $C_1$ to $C_4$ alkyl, $C_1$ to $C_4$ haloalkyl, $C_1$ to $C_4$ alkoxy, $C_1$ to $C_4$ alkylthio, $C_1$ to $C_4$ alkylsulfinyl, $C_1$ to $C_4$ alkylsulfonyl, $C_1$ to $C_4$ haloalkylthio, $C_1$ to $C_4$ haloalkylsulfinyl, $C_1$ to $C_4$ haloalkylsulfonyl, F, Cl or Br;
$R_9$ is H, F, Cl, $CH_3$, $OCH_3$, or $R_8$ and $R_9$, taken together, can be 3,4-methylenedioxy;
$R_{10}$, $R_{11}$, $R_{12}$ and $R_{13}$ are independently H, F, or Cl; and
$R_{14}$ is H, F, Cl, $OCH_3$, $OCH_2CH_3$, or $C_1$ to $C_2$ haloalkoxy.

Preferred compounds are those of Formula Ia wherein the substituent values are as previously defined:

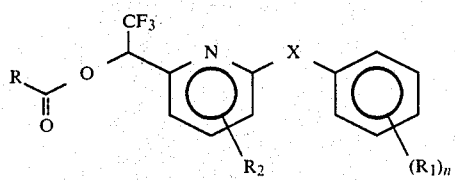

Ia

More preferred compounds are those of Formula Ia wherein:
X is O;
n is 1;
m is 1;
$R_1$ is H, $CH_3$, $CF_3$, $OCH_3$, $OCF_2H$, F, Cl, $SCH_3$, $SO_2CH_3$, $SCF_2H$, or $SO_2CF_2H$;
$R_2$ is H, F, or Cl;
$R_8$ is H, F, Cl, or $C_1$ to $C_2$ alkoxy;
$R_9$ is H; and
$R_{14}$ is H, F, Cl, $OCH_3$, $OCH_2CH_3$ or $OCF_2H$.

Most preferred compounds are those of Formula Ia wherein R is selected from R-A, R-B, R-D and R-E, the remaining substituents being as defined above with respect to "more preferred" compounds.

Preferred species wherein R is R-A are as follows:
[1-(6-Phenoxy-2-pyridinyl)-2,2,2-trifluoroethyl]3-(2-chloro-3,3,3-trifluoro-1-propenyl)-2,2-dimethylcyclopropanecarboxylate;
[1-(6-Phenoxy-2-pyridinyl)-2,2,2-trifluoroethyl]cis-3-(2,2-dichloroethenyl)-2,2-dimethylcyclopropanecarboxylate;
[1-(6-Phenoxy-2-pyridinyl)-2,2,2-trifluoroethyl]trans-3-(2,2-dichloroethenyl)-2,2-dimethylcyclopropanecarboxylate;
[1-(6-Phenoxy-2-pyridinyl)-2,2,2-trifluoroethyl]cis-3-(2,2-dibromoethenyl)-2,2-dimethylcyclopropanecarboxylate;
[1-(6-Phenoxy-2-pyridinyl)-2,2,2-trifluoroethyl](1R)-cis-3-(2,2-dibromoethenyl)-2,2-dimethylcyclopropanecarboxylate;
[1-(6-Phenoxy-2-pyridinyl)-(S)-2,2,2-trifluoroethyl]-(1R)-cis-3-(2,2-dibromoethenyl)-2,2-dimethylcyclopropanecarboxylate;
[1-(6-Phenoxy-2-pyridinyl)-2,2,2-trifluoroethyl]cis-3-(2-chloro-3,3,3-trifluoro-1-propenyl)-2,2-dimethylcyclopropanecarboxylate;
[1-(6-Phenoxy-2-pyridinyl)-(R)-2,2,2-trifluoroethyl]-(1S)-cis-3-(2-chloro-3,3,3-trifluoro-1-propenyl)-2,2-dimethylcyclopropanecarboxylate plus [1-[6-phenoxy-2-pyridinyl]-(S)-2,2,2-trifluoroethyl]-(1R)-cis-3-(2-chloro-3,3,3-trifluoro-1-propenyl)-2,2-dimethylcyclopropanecarboxylate;
[1-(6-Phenoxy-2-pyridinyl)-(S)-2,2,2-trifluoroethyl]-(1R)-cis-3-(2-chloro-3,3,3-trifluoro-1-propenyl)-2,2-dimethylcyclopropanecarboxylate;
[1-[6-(4-Fluorophenoxy)-2-pyridinyl]-2,2,2-trifluoroethyl]-cis-3-(2,2-dichloroethenyl)-2,2-dimethylcyclopropanecarboxylate; and
[1-[6-(4-Fluorophenoxy)-2-pyridinyl]-(R)-2,2,2-trifluoroethyl]-(1S)-cis-3-(2,2-dichloroethenyl)-2,2-dimethylcyclopropanecarboxylate plus [1-[6-(4-fluorophenoxy)-2-pyridinyl]-(S)-2,2,2-trifluoroethyl]-(1R)-cis-3-(2,2-dichloroethenyl)-2,2-dimethylcyclopropanecarboxylate.

Preferred species wherein R is R-B are as follows:
[1-[6-Phenoxy-2-pyridinyl]-2,2,2-trifluoroethyl]2,2,3,3-tetramethylcyclopropanecarboxylate; and
[1-[6-(4-Fluorophenoxy)-2-pyridinyl]-2,2,2-trifluoroethyl]-2,2,3,3-tetramethylcyclopropanecarboxylate.

A preferred species wherein R is R-D is [1-[6-phenoxy-2-pyridinyl]-2,2,2-trifluoroethyl]-(1R)-cis-2,2-dimethyl-3-(1,2,2,2-tetrabromoethyl)-cyclopropanecarboxylate.

A preferred species wherein R is R-E is [1-(6-Phenoxy-2-pyridinyl)-2,2,2-trifluoroethyl]4-chloro-α-(1-methylethyl)benzene acetate.

The optical isomer designations of the preferred species are based on analogy to other pyrethroids. Preparation of said compounds will be described hereafter.

Intermediates of this invention are compounds of Formula II and Formula III:

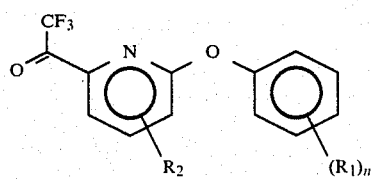

II

-continued

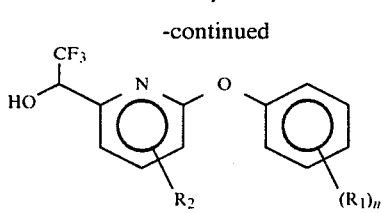

wherein $R_1$, $R_2$, and n are as defined previously.

Preferred intermediates are those employed to make the corresponding preferred insecticidal and acaricidal compounds, including:
1-(6-Phenoxy-2-pyridinyl)-2,2,2-trifluoroethanol;
1-(6-Phenoxy-2-pyridinyl)-(S)-2,2,2-trifluoroethanol; and
1-(6-Phenoxy-2-pyridinyl)-2,2,2-trifluoroethanone.

The agricultural compositions of this invention and the method for using them to control pests will be described in more detail in the Utility, Formulation and Application Sections of this disclosure.

The process of this invention concerned with making the novel ketone intermediates comprises the steps, in sequence, of:

(i) metallating the following phenoxy or thiophenoxy pyridinyl halide,

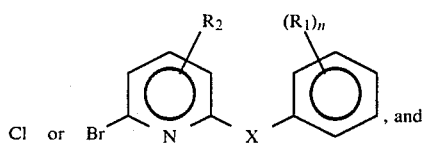

(ii) reacting the metallated product of step (i) with N,N-dimethyltrifluoroacetamide ($CF_3CON(CH_3)_2$) to form the corresponding phenoxypyridinyltrifluoroethanone wherein: $R_1$, $R_2$, X and n are as previously defined.

The described alcohol intermediates are made by (iii) reducing the ketone of step (ii), preferably with a hydride reducing agent, most preferably with $NaBH_4$.

DETAILS OF THE INVENTION

Compounds of Formula I can be prepared by the reaction of pyridine alcohols of Formula III with any of the conventional pyrethroid acid chlorides of Formula IV. Typical reactions involve the combination of equimolar amounts of III and IV in the presence of an amine base such as triethylamine or pyridine at temperatures generally in the range of 0° to 40° C. Suitable solvents include ether, tetrahydrofuran, chloroform and benzene. For clarity, only the 2,6-isomer of III is depicted; however, it is understood that the procedures that follow apply to each of the pyridine isomers disclosed.

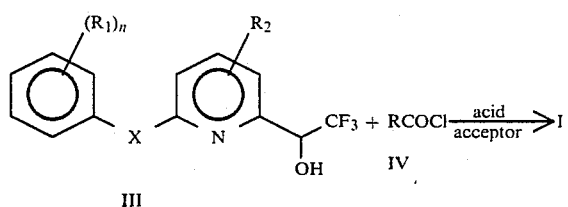

An alternate approach to compounds of Formula I, which may be preferred where the intermediate acid chloride of Formula IV is of low stability, is the reaction of a pyrethroid acid of Formula V with a pyridine of Formula VI, wherein L represents a suitable leaving group such as Cl, Br, methanesulfonyloxy and p-tolylsulfonyloxy. For example, equimolar amounts of V and VI can be combined in the presence of an alkali metal carbonate or alkali metal bicarbonate in a polar aprotic solvent such as dimethylformamide or dimethylsulfoxide to afford the esters of Formula I. The reaction can be conducted at temperatures ranging from about 0° to 80° C., although temperatures in the range of 20° to 60° C. are preferred.

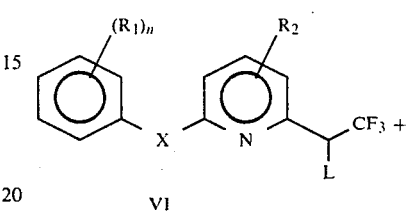

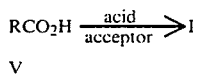

An alternate approach to compounds of Formula I is the reaction of an alcohol of Formula III with an acid of Formula V in the presence of a dehydrating agent such as dicyclohexylcarbodiimide (DCC). The reaction is conducted in a solvent such as ether or methylene chloride and generally in the presence of an amine base such as pyridine.

It is to be recognized that compounds of Formula I include a number of both geometrical and optical isomers which may differ dramatically in biological activity. In some instances, it may be desirable to obtain compounds which are geometrically and/or optically pure or which are enriched in one or more of the possible isomers.

It is well recognized that compounds of the pyrethroid class require a specific spatial orientation for optimum levels of activity. Generally, a single enantiomer is responsible for most of the observed activity (see, e.g., "Recent Advances in the Chemistry of Insect Control", ed. Janes, Royal Society of Chemistry, Burlington House, 1985, p. 26). Based on the known spatial requirements, compounds of the present invention would be predicted to exhibit their highest levels of activity for compounds derived from the S-alcohol of Formula III. The absolute configuration of the more active isomer of the acid portion (V) is dependent on the specific acid used (where R is R-A through R-F). However, for each of the acid groups the same spatial orientation is required for optimum activity.

As an example, an isomer mixture of Formula I derived from a racemic alcohol of Formula III and a racemic acid of Formula V (where R is R-A with a cis cyclopropane) consists of a mixture of racemic diastereomers. The diastereomeric mixture can be separated by either fractional recrystallization or chromatography. The enantiomeric pair containing the (1R)-cis-α-S enantiomer is expected to show the greater level of activity (note that in the designation (1R)-cis-α-S that (1R)-cis refers to a cis cyclopropane wherein carbon number 1 is of the R configuration, and α-S refers to the asymmetric center α to the pyridine ring and possessing the S configuration).

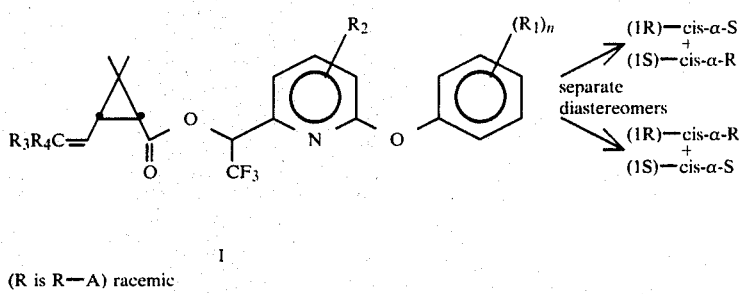

I (R is R—A) racemic

Resolution of the alcohol of Formula III can be accomplished by any of a number of suitable methods known in the art for the resolution of alcohols in general. One such method involves reaction of racemic III with an optically active resolving agent, such as (R)-(+)-1-phenylethyl isocyanate, chromatographic separation of the diastereomeric carbamates VII and, finally, regeneration of the resolved alcohol. Other suitable resolving agents include R-(−)-1-(1-naphthyl)ethyl isocyanate and (R)-(+)-α-methoxy-α-(trifluoromethyl)phenylacetic acid.

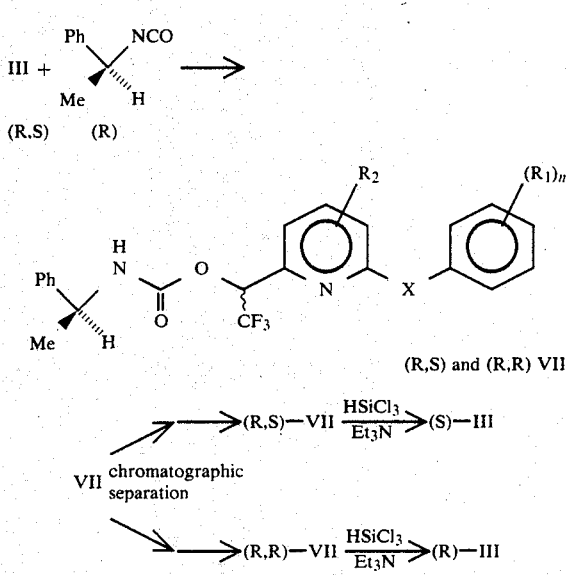

Novel intermediates of Formula VI can be prepared from the alcohols of Formula III by any of the known methods for conversion of a hydroxy group to a suitable leaving group. For example, the methanesulfonates of Formula VI (L is $OSO_2CH_3$) can be prepared by the reaction of methanesulfonyl chloride with compounds of Formula III in the presence of an amine base such as triethylamine. Chlorides of Formula VI (where L is Cl) can be prepared by reaction of III with, for example, thionyl chloride. Variants of these reactions are well documented in the chemical literature and would be known to one skilled in the art.

Pyridines of Formula III are available in two steps from halopyridines VIII via (a) introduction of the trifluoroacetyl group to form II and (b) hydride reduction of II to the alcohol III:

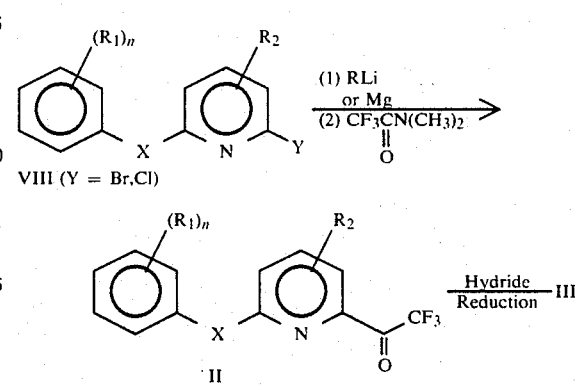

Reaction of VIII (Y=Br) with an alkyl lithium, such as n-butyllithium, to effect metal-halogen exchange, at temperatures ranging from 0° to −100° C. and in a solvent such as tetrahydrofuran or ether, followed by reaction of the preformed pyridinyl lithium salt with N,N-dimethyltrifluoroacetamide or an alkali metal salt of trifluoroacetic acid affords the novel trifluoroacetylpyridines of Formula II. Alternatively, treatment of VIII with magnesium to effect Grignard formation, at temperatures ranging from 60° to −80° C. and in solvents such as tetrahydrofuran or ether, followed by reaction with N,N-dimethyltrifluoroacetamide affords the trifluoroacetylpyridines of Formula II. These in turn are readily reduced to the alcohols of Formula III by any of a number of the standard methods, examples of which include the hydride reducing agents lithium aluminum hydride and sodium borohydride.

The intermediate halopyridines (VIII) can be prepared from 2,6-dihalopyridines and an optionally substituted phenol or thiophenol. As an example, reaction of equimolar quantities of

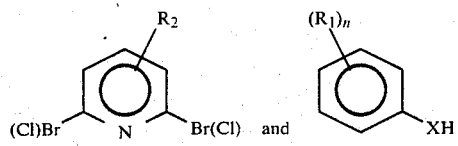

in a solvent such as acetone, methyl ethyl ketone, acetonitrile, tetrahydrofuran or dimethylformamide in the presence of a base such as potassium carbonate or sodium hydride affords the 2-halopyridinyl ethers of Formula VIII.

Compounds of Formula IV and V are well known in the chemical literature. Those skilled in the art will recognize these to be, or to be derived from, the acid component of the synthetic pyrethroid insecticides. Selected references to these are as follows: For compounds where R is R-A see South African Patent Application No. 73/3528, U.S. Pat. No. 4,332,815 and U.S. Pat. No. 4,157,397; where R is R-B see Ger. Offen. Pat. No. 2,407,024 and U.S. Pat. No. 4,221,799; where R is R-C see Jap. Pat. Appl. No. J5 7,040,463; where R is R-D see Ger. Pat. Nos. 2,742,546 and 2,742,547; where R is R-E see U.S. Pat. No. 4,061,968; and where R is R-F see European Pat. Appl. No. 002620 and U.S. Pat. No. 4,360,690.

The following Examples illustrate the invention.

EXAMPLE 1

Step A

2-Bromo-6-phenoxypyridine

To a solution of 6.5 g (0.135 mol) of 50% sodium hydride in 75 ml of dimethylformamide at 0° C. and under $N_2$ was added a solution of 11.9 g (0.127 mol) of phenol in 75 ml of dimethylformamide. Once dropwise addition was complete, 30.0 g (0.127 mol) of 2,6-dibromopyridine was added in one portion and the mixture was heated at 60° to 65° C. for 18 hours. The mixture was then cooled and partitioned between ether and 1N aqueous NaOH. The ether extracts were washed two times with aqueous $NaHCO_3$, dried over $MgSO_4$, filtered and concentrated under vacuum. The solid residue was slurried in hexane, filtered and dried to afford 25.1 g (79%) of the title compound as a white powder: m.p. 83° to 86° C.; $^1$H NMR ($CDCl_3$) δ 6.70 (d, 1H), 7.0–7.5 (m, 7H).

Step B

2,2,2-Trifluoro-1-(6-phenoxy-2-pyridinyl)ethanone

A solution of 12.5 g (0.05 mol) of the 2-bromo-6-phenoxypyridine of Step A in 100 ml of dry tetrahydrofuran was cooled under $N_2$ to −70° C. To this solution was added 20 ml (0.052 mol) of 2.6M n-butyllithium in hexane at such a rate that the reaction temperature was maintained below −60° C. The reaction was stirred 5 minutes and then 7.75 g (0.055 mol) of N,N-dimethyltrifluoroacetamide in 15 ml of tetrahydrofuran was added at such a rate that the reaction was maintained below −60° C. Once addition was complete, the −70° C. bath was removed and the reaction was stirred for one hour with gradual warming. After this time, 50 ml of 5% aqueous $NaHCO_3$ were added and the tetrahydrofuran was removed under vacuum. The aqueous residue was extracted twice with chloroform, and the chloroform extracts were then dried over $MgSO_4$, filtered and concentrated to yield 13.6 g of an orange oil. Chromatography on silica gel afforded 7.71 g (57%) of the title compound as a yellow oil: $^1$H NMR and IR suggest the title compound exists in the form of a hydrate: $^1$H NMR δ 4.84 (s), 7.0–8.0 (m); IR (neat) 1588, 1735, 3400 cm$^{-1}$.

Step C

6-Phenoxy-α-(trifluoromethyl)-2-pyridinemethanol

To a solution of 10.0 g (0.0375 mol) of the 2,2,2-trifluoro-1-(6-phenoxy-2-pyridinyl)ethanone of Step B in 100 ml of ethanol at 0° C. was added 1.5 g (0.0395 mol) of sodium borohydride portionwise over 5 to 10 minutes. The reaction was then warmed to room temperature and stirred overnight. After this time, the reaction was quenched with 1N aqueous HCl, neutralized with aqueous $NaHCO_3$ and extracted with chloroform. The chloroform extracts were dried over $MgSO_4$, filtered and concentrated to afford a yellow oil which solidified on standing to a waxy solid. Recrystallization from 4:1 hexane-ether afforded 6.13 g (60%) of the title compound as a white powder: m.p. 75° to 77° C.; $^1$H NMR ($CDCl_3$) δ 4.67 (d, 1H), 4.92 (dq, 1H), 6.9–7.5 (m, 7H), 7.78 (t, 1H); IR (Nujol) 1570, 1600, 3390 cm$^{-1}$.

Step D cis-[1-(6-Phenoxy-2-pyridinyl)-2,2,2-trifluoroethyl]3-(2,2-dichloroethenyl)-2,2-dimethylcyclopropanecarboxylate To a solution of 2.04 g (7.6 mmol) of the 6-phenoxy-α-(trifluoromethyl)-2-pyridinemethanol of Step C and 1.72 g (7.6 mmol) of cis-3-(2,2-dichloroethenyl)-2,2-dimethylcyclopropanecarbonyl chloride in 30 ml of dry tetrahydrofuran was added 2.0 ml (14.2 mmol) of triethylamine. The reaction was stirred for 72 hours. The precipitated triethylamine hydrochloride was then filtered off and the filtrate was concentrated under vacuum. The residue was chromatographed through silica gel and then distilled bulb to bulb (bp 155° C., 0.2 mm) to afford 2.61 g (74%) of the title compound as a clear, colorless oil, which was obtained as a mixture of diastereomers as indicated by the $^1$H NMR spectrum: $^1$H NMR ($CDCl_3$) δ 1.14, 1.24, 1.26, 1.29 (4×s, 6H), 2.0–2.2 (m, 2H), 6.0–6.2 (m, 2H), 6.90 (d, 1H), 7.1–7.5 (m, 6H), 7.75 (t, 1H); IR (neat) 1742 cm$^{-1}$.

EXAMPLE 2

[1-(6-Phenoxy-2-pyridinyl)-2,2,2-trifluoroethyl]4-chloro-α-(1-methylethyl)benzeneacetate Application of the procedure of Example 1 afforded 0.20 g (51%) of the title compound as a clear colorless oil. The $^1$H NMR spectrum indicated the title compound was obtained as a mixture of diastereomers: $^1$H NMR ($CDCl_3$) δ 0.73 (d, 3H), 1.03 (2×d, 3H), 2.3 (m, 1H), 3.30 (2×d, 1H), 6.05 (quintet, 1H), 6.8 (2×d, 1H), 7.0–7.7 (m, 7H); IR (neat) 1750 cm$^{-1}$.

EXAMPLE 3

[1-(6-Phenoxy-2-pyridinyl)-2,2,2-trifluoroethyl]3-(2-chloro-3,3,3-trifluoro-1-propenyl)-2,2-dimethylcyclopropanecarboxylate Application of the procedure of Example 1 afforded 0.32 g (72%) of the title compound as a clear colorless oil. The $^1$H NMR spectrum indicated the product was obtained as an isomeric mixture: $^1$H NMR δ 1.1–1.3 (m, 6H), 1.9–2.5 (m, 2H), 6.0–6.2 (m, 2H), 6.89 (d, 1H), 7.1–7.5 (m, 6H), 7.74 (t, 1H); IR (neat) 1750 cm$^{-1}$.

EXAMPLE 4 cis-[(1-(6-Phenoxy-2-pyridinyl)-2,2,2-trifluoroethyl]3-(2-chloro-3,3,3-trifluoro-1-propenyl)-2,2-dimethylcyclopropanecarboxylate Application of the procedure of Example 1 (Step D) with 0.79 g of cis-3-(2-chloro-3,3,3-trifluoro-1-propenyl)-2,2-dimethylcyclopropane carbonyl chloride afforded 1.0 g of the title compound as a clear, colorless oil. The $^1$H NMR indicated the compound was obtained as a 1:1 mixture of diastereomers. $^1$H NMR ($CDCl_3$) δ 1.17, 1.27, 1.31, 1.34 (4×s, 6H), 2.1 (m, 2H), 6.05, 6.10 (2×q, 1H), 6.78, 6.82 (2×d, 1H), 6.87 (d, 1H), 7.1–7.9 (m, 7H). IR (neat) 1748 cm$^{-1}$.

EXAMPLE 5

Separation of the Diastereomeric Pairs of cis-1-[(6-phenoxy-2-pyridinyl)-2,2,2-trifluoroethyl]3-(2-chloro-3,3,3-trifluoro-1-propenyl)-2,2-dimethylcyclopropanecarboxylate Chromatographic separation (silica gel, 2% ethyl acetate/hexane) of 8.4 g of a diastereomeric mixture of Example 4 afforded 2.71 g of diastereomer A ($R_f$ 0.45, 5% ethyl acetate/hexane), m.p. 100° to 101° C., and 2.71 g of diastereomer B ($R_f$ 0.37, 5% ethyl acetate/hexane), m.p. 66° to 68° C. The higher $R_f$ diastereomer (A) is designated as the (1R)-cis-α-R/(1S)-cis-α-S enantiomeric pair and the lower $R_f$ diastereomer (B) is designated as the (1R)-cis-α-S/(1S)-cis-α-R enantiomeric pair.

Diastereomer A: $^1$H NMR (CDCl$_3$) δ 1.26 (s, 3H), 1.34 (s, 3H), 2.13 (d, 1H), 2.25 (t, 1H), 6.05 (q, 1H), 6.75 (d, 1H), 6.86 (d, 1H), 7.1–7.5 (m, 6H), 7.75 (t, 1H). IR (Nujol ®) 1738 cm$^{-1}$.

Diastereomer B: $^1$H NMR (CDCl$_3$) δ 1.17 (s, 3H), 1.31 (s, 3H), 2.15 (d, 1H), 2.28 (t, 1H), 6.02 (q, 1H), 7.01 (d, 1H), 7.2 (m, 4H), 7.40 (t, 1H), 7.74 (t, 1H). IR (neat) 1735 cm$^{-1}$.

Assignment of configuration for diastereomer B as the (1R)-cis-α-S/(1S)-cis-α-R enantiomeric pair was based on the observation that this diastereomer was considerably more active in the biological tests. In the Examples that follow, the diastereomers possessing the highest levels of activity were designated to contain the (1R)-cis-α-S enantiomer and its optical isomer.

EXAMPLE 6 trans-1-[(6-Phenoxy-2-pyridinyl)-2,2,2-trifluoroethyl]3-(2-chloro-3,3,3-trifluoro-1-propenyl)-2,2-dimethylcyclopropane carboxylate Application of the procedure of Example 1 (Step D) with 4.22 g of trans-3-(2-chloro-3,3,3-trifluoro-1-propenyl)-2,2-dimethylcyclopropanecarbonyl chloride afforded a 1:1 diastereomeric mixture of the title compound, the components of which were separated by chromatography (silica gel, 2% ethyl acetate/hexane) and distilled bulb to bulb to afford 2.96 g of diastereomer A ($R_f$ 0.45, 5% ethyl acetate/hexane) and 2.92 g of diastereomer B ($R_f$ 0.39, 5% ethyl acetate/hexane).

Diastereomer A: $^1$H NMR (CDCl$_3$) δ 1.28 (s, 3H), 1.32 (s, 3H), 1.92 (d, 1H), 2.4 (m, 1H), 6.1 (m, 2H), 6.85 (d, 1H), 7.1–7.5 (m, 6H), 7.75 (t, 1H). IR (neat) 1638 cm$^{-1}$.

Diastereomer B: $^1$H NMR (CDCl$_3$) δ 1.23 (s, 3H), 1.25 (s, 3H), 1.94 (d, 1H), 2.44 (m, 1H), 6.06 (q, 1H), 6.17 (d, 1H), 6.88 (d, 1H), 7.1–7.5 (m, 6H), 7.74 (t, 1H). IR (neat) 1636 cm$^{-1}$.

EXAMPLE 7

Step A

[R-(R*,R*)]- and [S-(R*,S*)]-[1-(6-phenoxy-2-pyridinyl)-2,2,2-trifluoroethyl]-1-phenylethylcarbamate A stirred solution of 2.40 g (8.91 mmol) of α-trifluoromethyl-6-phenoxy-2-pyridinemethanol, 1.38 g (9.36 mmol) of (R)-(+)-1-phenylethyl isocyanate, and 22 mg (0.18 mmol) of 4-dimethylaminopyridine in 9 ml of benzene under a nitrogen atmosphere was heated at 50° C. for 17 hours. The reaction mixture was then diluted with 150 ml of ether and washed with 25 ml of 1N aqueous HCl, 25 ml of saturated aqueous NaHCO$_3$, and 25 ml of saturated aqueous NaCl. The organic layer was dried (MgSO$_4$) and concentrated under reduced pressure. Repeated chromatography of the residue on silica gel with benzene afforded first 1.77 g (48%) of the [R-(R*,R*)] diastereomer: $R_f$=0.10 (SiO$_2$, benzene); $^1$H NMR (CDCl$_3$) δ 1.52 (d, 6.8 Hz, 3H), 4.83 (quintet, 7.1 Hz, 1H), 6.01 (q, 6.1 Hz, 1H), 6.83 (d, 8.2 Hz, 1H), 7.11–7.37 (br m, 12H), and 7.68 (t, 7.8 Hz, 1H); and then 1.77 g (48%) of the [S-(R*,S*)] diastereomer: $R_f$=0.09 (SiO$_2$, benzene); $^1$H NMR (CDCl$_3$) δ 1.47 (d, 6.8 Hz, 3H), 4.80 (quintet, 7.0 Hz, 1H), 5.98 (q, 6.9 Hz, 1H), 6.86 (d, 8.3 Hz, 1H), 7.13–7.42 (br m, 12H), and 7.72 (t, 7.8 Hz, 1H).

Step B (S)-(+)-6-Phenoxy-α-trifluoromethyl-2-pyridinemethanol

A stirred solution of 1.28 g (3.08 mmol) of the [S-(R*,S*)] carbamate from Step A, 0.52 ml (380 mg, 3.7 mmol) of triethylamine, and 0.34 ml (460 mg, 3.4 mmol) of trichlorosilane in 12 ml of toluene under a nitrogen atmosphere was heated at 60° C. for 2 hours. The reaction mixture was then diluted with 50 ml of saturated aqueous NH$_4$Cl and extracted with ether (3×25 ml). After being dried (MgSO$_4$), the combined organic extracts were concentrated under reduced pressure and chromatography of the residue on 20 g of silica gel with 1:15 ethyl acetate/hexane afforded 667 mg (81%) of the title compound as a white solid melting at 51.5°–53.5° C.: $[α]_D^{22}$=+2.0° (CHCl$_3$, c 1.00) and $[α]_{365}^{22}$=+4.8° (CHCl$_3$, c 1.00). The spectral and chromatographic properties of this material were identical to those of racemic material prepared in Example 1 (Step C).

Step C (S)-[1-(6-Phenoxy-2-pyridinyl)-2,2,2-trifluoroethyl](1R)-cis-(2-chloro-3,3,3-trifluoro-1-propenyl)-2,2-dimethylcyclopropanecarboxylate (Enantiomer B)

To a stirred solution of 612 mg (2.52 mmol) of cis-3-(2-chloro-3,3,3-trifluoro-1-propenyl)-2,2-dimethylcyclopropanecarboxylic acid, 647 mg (2.40 mmol) of the (S)-(+)-6-phenoxy-α-trifluoromethyl-2-pyridinemethanol from Step B, and 37 mg (0.30 mmol) of 4-dimethylaminopyridine in 6.0 ml of CH$_2$Cl$_2$ cooled to 0° C. under a nitrogen atmosphere was added 620 mg (3.00 mmol) of 1,3-dicyclohexylcarbodiimide. After 2 hours at 0° C., the reaction mixture was diluted with 50 ml of hexane and filtered. The filtrate was concentrated under reduced pressure and chromatography of the residue on 100 g of silica gel with 1:60 ether/hexane afforded first 608 mg (51%) of Enantiomer A, assigned the (1S)-cis-α-S configuration, as a colorless oil: $[α]_D^{22}$=−14.5° (CHCl$_3$, c 1.20) and $[α]_{365}^{22}$=104.7° (CHCl$_3$, c 1.20).

Further elution afforded 573 mg (48%) of Enantiomer B, assigned the (1R)-cis-α-S configuration, as a colorless oil: $[α]_D^{22}$=+48.4° (CHCl$_3$, c 1.08) and $[α]_{365}^{22}$=+183.8° (CHCl$_3$, c 1.08). The spectral and chromatographic properties of this material were idential to those of racemic material prepared in Example 5.

EXAMPLE 8

[1-(6-Phenoxy-2-pyridinyl)-2,2,2-trifluoroethyl]trans-3-(2,2-dichloroethenyl)-2,2-dimethylcyclopropanecarboxylate Application of the procedure of Example 1 (Step D) with 1.9 g of trans-3-(2,2-dichloroethenyl)-2,2-dimethylcyclopropane carbonyl chloride afforded 1.78 g (48%) of the title compound as a viscous yellow oil. The $^1$H NMR indicated the product to consist of a 1:1 mixture of diastereomers. $^1$H NMR (CDCl$_3$) δ 1.20, 1.21, 1.24, 1.28 (4×s, 6H), 1.8 (m, 1H), 2.3 (m, 1H), 5.64, 5.66 (2×d, 1H), 6.1 (m, 1H), 6.88 (d, 1H), 7.1–7.8 (m, 7H). IR (neat) 1750 cm$^{-1}$.

EXAMPLE 9

[1-[6-(4-Fluorophenoxy)-2-pyridinyl]-2,2,2-trifluoroethyl]-cis-3-(2,2-dichloroethenyl)-2,2-dimethylcyclopropane carboxylate A solution of 12 g of 6-(4-fluorophenoxy)-α-trifluoromethyl-2-pyridinemethanol and 9.7 g of cis-3-(2,2-dichloroethenyl)-2,2-dimethylcyclopropanecarbonyl chloride in 100 ml of dry THF under an atmosphere of nitrogen was cooled to 10° to 15° C. and treated with 6.5 ml of triethylamine, added in a dropwise manner. The reaction mixture was stirred at room temperature for approximately 14 hours and was then filtered. The filtrate was concentrated under vacuum to afford 20.8 g of a light orange semisolid, which was shown in TLC analysis (silica gel; 10% ethyl acetate/hexanes) to consist of two components. Purification by flash chromatography gave the title compound as a mixture of diastereomers, m.p. 69°–72° C.; NMR (200 MHz, CDCl$_3$): δ 1.14 (1.2H, s), 1.24 (1.8H, s), 1.27 (1.2H, s), 1.30 (1.8H, s), 2.0–2.2 (2H, m), 5.95–6.2 (2H, m), 6.89 (1H, d, J=8 Hz), 7.05–7.2 (5H, m), 7.75 (1H, t, J=8 Hz).

EXAMPLE 10

Separation of the diastereomers of [1-[6-(4-Fluorophenoxy)-2-pyridinyl]-2,2,2-trifluoroethyl]-cis-3-(2,2-dichloroethenyl)-2,2-dimethylcyclopropanecarboxylate A 2-gram sample of the above was subjected to chromatographic purification. Elution with 5% ethyl acetate/hexanes gave 800 mg of the higher R$_f$ diastereomer (A) (R$_f$ 0.57, 10% ethyl acetate/hexane) as a white solid, m.p. 97° to 99° C.; NMR (200 MHz, CDCl$_3$): δ 1.24 (3H, s), 1.30 (3H, s), 2.01 (1H, d, J=8 Hz), 2.12 (1H, t, J=8 Hz), 6.05 (1H, q, J=7 Hz), 6.08 (1H, d, J=8 Hz), 6.89 (1H, d, J=8 Hz), 7.05–7.2 (5H, m), 7.75 (1H, t, J=8 Hz); the lower R$_f$ diastereomer (B) (R$_f$ 0.50, 10% ethyl acetate/hexane) was obtained as a white solid (700 mg), m.p. 78.5°–81° C.; NMR (200 MHz, CDCl$_3$): δ 1.14 (3H, s), 1.27 (3H, s), 2.01 (1H, d, J=8 Hz, 2.14 (1H, t, J=8 Hz), 6.0 (1H, q, J=7 Hz), 6.15 (1H, d, J=8 Hz), 6.89 (1H, d, J=8 Hz), 7.05–7.2 (5H, m), 7.75 (1H, t, J=8 Hz).

Diastereomer A is assigned the (1R)-cis-α-R/(1S)-cis-α-S configuration and diastereomer B is assigned the (1R)-cis-α-S/(1S)-cis-α-R configuration.

EXAMPLE 11

1-R-cis-[1-(6-Phenoxy-2-pyridinyl)-2,2,2-trifluoroethyl 3-(2,2-dibromoethenyl)-2,2-dimethylcyclopropanecarboxylate Application of the procedure of Example 1 (Step D) with 4.5 g of 1-R-cis-(2,2-dibromoethenyl)-2,2-dimethylcyclopropanecarbonyl chloride afforded 3.59 g of the title compound as a yellow oil. The $^1$H NMR indicated the product consisted of a 1:1 mixture of diastereomers. $^1$H NMR (CDCl$_3$) δ 1.15, 1.25, 1.27, 1.29 (4×s, 6H), 2.02 (m, 2H), 6.03 (m, 1H), 6.65 (m, 1H), 6.85 (d, 1H), 7.1–7.5 (m, 6H), 7.78 (m, 1H). IR (neat) 1745 cm$^{-1}$.

EXAMPLE 12

1-R-cis-[1-(6-Phenoxy-2-pyridinyl)-2,2,2-trifluoroethyl]2,2-dimethyl-3-(1,2,2,2-tetrabromoethyl)cyclopropanecarboxylate A solution of 1.76 g (3.2 mmol) of the ester of Example 11 in 10 ml of carbon tetrachloride was cooled to 0° C. under N$_2$. To this solution was added 0.2 ml (3.9 mmol) of bromine and the reaction was then warmed to room temperature. After five days solvent and excess bromine was removed in vacuo affording the title compound as a viscous oil. $^1$H NMR analysis indicated a four component mixture of diastereomers. $^1$H NMR (CDCl$_3$) δ 1.1–1.5 (m, 6H), 1.9–2.1 (m, 2H), 4.9–5.4 (m, 1H), 6.1 (m, 1H), 6.9 (m, 1H), 7.1–7.9 (m, 7H). IR (neat) 1730 cm$^{-1}$.

EXAMPLE 13

[1-(6-Phenoxy-2-pyridinyl)-2,2,2-trifluoroethyl]2,2,3,3-tetramethylcyclopropanecarboxylate Application of the procedure of Example 1 (Step D) with 1.0 g of 2,2,3,3-tetramethylcyclopropane carbonyl chloride afforded 1.0 g of the title compound as a yellow oil. $^1$H NMR (CDCl$_3$) δ 1.16 (s, 3H), 1.21 (s, 3H), 1.23 (s, 6H), 1.38 (S, H), 6.06 (q, 1H), 6.86 (d, 1H), 7.1–7.5 (m, 6H), 7.75 (t, 1H). IR (neat) 1750 cm$^{-1}$.

EXAMPLE 14

[1-(5-Phenoxy-3-pyridinyl)-2,2,2-trifluoroethyl]cis-3-(2-chloro-3,3,3-trifluoro-1-propenyl)-2,2-dimethylcyclopropanecarboxylate To a stirred solution of 265 mg (1.09 mmol) of cis-3-(2-chloro-3,3,3-trifluoro-1-propenyl)-2,2-dimethylcyclopropanecarboxylic acid, 265 mg (0.984 mmol) of 5-phenoxy-α-trifluoromethyl-3-pyridinemethanol, and 15 mg (0.12 mmol) of 4-dimethylaminopyridine (DMAP) in 3.0 ml of CH$_2$Cl$_2$ cooled to 0° C. under a nitrogen atmosphere was added 254 mg (1.23 mmol) of 1,3-dicyclohexylcarbodiimide (DCC). After 1 hour at 0° C., the mixture was diluted with 20 ml of hexane and filtered. The filtrate was concentrated under reduced pressure and chromatography of the residue on 50 g of silica gel with 1:20 ethyl acetate/hexane afforded first 227 mg (47%) of diastereomer A assigned the (1R)-cis-α-R/(1S)-cis-α-S configuration: R$_f$=0.10 (silica gel, 1:20 ethyl acetate/hexane); $^1$H NMR (CDCl$_3$) δ 1.29 (s, 3H), 1.36 (s, 3H), 2.11 (d, 8.2 Hz, 1H), 2.25 (t, 8.6 Hz, 1H), 6.17 (q, 6.2 Hz, 1H), 6.76 (d, 9.3 Hz, 1H), 7.04 (d, 8.6 Hz, 2H), 7.21 (m, 1H), 7.40 (t, 8.0 Hz, 2H), 7.40 (s, 1H), and 8.43 (s, 2H).

Further elution then afforded 206 mg (42%) of diastereomer B, assigned the (1R)-cis-α-S/(1S)-cis-α-R configuration: R$_f$=0.06 (SiO$_2$, 1:20 ethyl acetate/hexane); $^1$H NMR (CDCl$_3$) δ 1.17 (s, 3H), 1.32 (s, 3H), 2.13 (d, 8.2 Hz, 1H), 2.28 (t, 8.6 Hz, 1H), 6.10 (q, 6.9 Hz, 1H), 6.78 (d, 9.0 Hz, 1H), 7.05 (d, 8.3 Hz, 2H), 7.21 (m, 1H), 7.37 (s, 1H), 7.41 (t, 8.0 Hz, 2H), and 8.43 (s, 2H).

EXAMPLE 15

[1-(2-Phenoxy-4-pyridinyl)-2,2,2-trifluoroethyl]cis-3-(2-chloro-3,3,3-trifluoro-1-propenyl)-2,2-dimethylcyclopropanecarboxylate Application of the procedure in Example 8 (Step C) with 215 mg (0.886 mmol) of the carboxylic acid, 215 mg (0.799 mmol) of 2-phenoxy-α-trifluoromethyl-4-pyridinemethanol, 12 mg (0.098 mmol) of DMAP, and 206 mg (0.998 mmol) of DCC in 2.4 ml of CH$_2$Cl$_2$ cooled to 0° C. afforded, after workup and chromatography, first 184 mg (47%) of diastereomer A, assigned the (1R)-cis-α-R/(1S)-cis-α-S configuration: R$_f$=0.12 (SiO$_2$, 1:20 ethyl acetate:hexane); $^1$H NMR (CDCl$_3$) δ 1.32 (s, 3H), 1.38 (s, 3H), 2.17 (d, 8.1 Hz, 1H), 2.28 (t, 8.6 Hz, 1H), 6.14 (q, 6.6 Hz, 1H), 6.77 (d, 9.0 Hz, 1H), 7.03 (s, 1H), 7.06 (d, 5.0 Hz, 1H), 7.15 (d, 7.3 Hz, 2H), 7.23 (m, 1H), 7.43 (t, 8.0 Hz, 2H), and 8.23 (d, 5.0 Hz, 1H); and then 171 mg (43%) of diastereomer B, assigned the (1R)-cis-α-S/(1S)-cis-α-R configuration: R$_f$=0.08 (SiO$_2$, 1:20 ethyl acetate/hexane); $^1$H NMR (CDCl$_3$) δ 1.21 (s, 3H), 1.36 (s, 3H), 2.18 (d, 8.1 Hz, 1H), 2.32 (t, 8.6 Hz, 1H), 6.07 (q, 6.7 Hz, 1H), 6.80 (d, 9.0 Hz, 1H), 7.00 (s, 1H), 7.05 (d, 5.0 Hz, 1H), 7.15 (d, 8.6 Hz, 2H), 7.24 (m, 1H), 7.43 (t, 7.8 Hz, 2H), and 8.24 (d, 5.0 Hz, 1H).

EXAMPLE 16

[1-(4-Phenoxy-2-pyridinyl)-2,2,2-trifluoroethyl]cis-3-(2,2-dichloroethenyl)-2,2-dimethylcyclopropanecarboxylate To a stirred solution of 280 mg (1.04 mmol) of 4-phenoxy-α-trifluoromethyl-2-pyridinemethanol and 0.29 ml (210 mg, 2.08 mmol) of triethylamine in 2.6 ml of CH$_2$Cl$_2$ cooled to 0° C. under a nitrogen atmosphere was added 284 mg (1.25 mmol) of cis-3-(2,2-dichloroethenyl)-2,2-dimethylcyclopropanecarbonyl chloride. After 1 hour at 0° C., the reaction mixture was allowed to warm to room temperature for 15 hours. The mixture was then diluted with 60 ml of saturated aqueous NaHCO$_3$ and extracted with CH$_2$Cl$_2$ (2×25 ml). After being dried (MgSO$_4$), the combined extracts were concentrated under reduced pressure and chromatography of the residue on 50 g of silica gel with 1:15 ethyl acetate/hexane afforded first 215 mg (45%) of diastereomer A, assigned the (1R)-cis-α-R/(1S)-cis-α-S configuration: R$_f$=0.12 (SiO$_2$, 1:15 ethyl acetate/hexane); $^1$H NMR (CDCl$_3$) δ 1.26 (s, 3H), 1.30 (s, 3H), 2.03 (d, 8.0 Hz, 1H), 2.13 (t, 8.0 Hz, 1H), 6.11 (d, 8.1 Hz, 1H), 6.17 (q, 6.6 Hz, 1H), 6.82 (dd, 2.4 Hz, 6.0 Hz, 1H), 7.08 (br s, 1H), 7.11 (d, 8.1 Hz, 2H), 7.29 (m, 1H), 7.46 (t, 7.7 Hz, 2H), and 8.47 (d, 6.0 Hz, 1H).

Further elution then afforded 185 mg (39%) of diastereomer B, assigned the (1R)-cis-α-S/(1S)-cis-α-R configuration: R$_f$=0.08 (SiO$_2$, 1:15 ethyl acetate/hexane);

$^1$H NMR (CDCl$_3$) δ 1.14 (s, 3H), 1.26 (s, 3H), 2.03 (d, 8.0 Hz, 1H), 2.14 (t, 8.0 Hz, 1H), 6.10 (q, 7.3 Hz, 1H), 6.19 (d, 8.0 Hz, 1H), 6.82 (dd, 2.3 Hz, 5.3 Hz, 1H), 7.03 (br s, 1H), 7.10 (d, 8.6 Hz, 2H), 7.29 (m, 1H), 7.46 (t, 8.2 Hz, 2H), and 8.48 (d, 5.2 Hz, 1H).

By the general procedure described herein, one can prepare the compounds of Tables 1 to 9 (insecticides and acaricides) and Tables 10 and 11 (intermediates).

General Structures for Tables 1 to 9

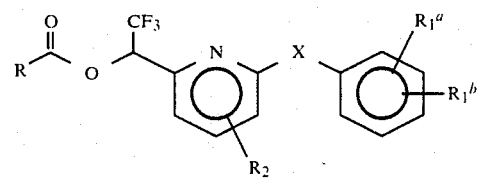

| Table | R |
|---|---|
| 1 | R—A |
| 2 | R—B |
| 3 | R—C |
| 4 | R—D |
| 5 | R—E |
| 6 | R—F |

7

8

9

TABLE 1

| X | R$_1$$^a$ | R$_1$$^b$ | R$_2$ | R$_3$ | R$_4$ | Cyclopropane Geometry | Dia.* | Phys. Prop. |
|---|---|---|---|---|---|---|---|---|
| O | 4-Cl | H | H | Cl | Cl | cis/trans | | |
| O | 4-F | H | H | Cl | Cl | cis/trans | | |
| O | 4-Br | H | H | Cl | Cl | cis/trans | | |
| O | 4-CF$_3$ | H | H | Cl | Cl | cis/trans | | |
| O | 4-SCH$_3$ | H | H | Cl | Cl | cis/trans | | |
| O | 4-S—n-C$_4$H$_9$ | H | H | Cl | Cl | cis/trans | | |
| O | 4-OCH$_3$ | H | H | Cl | Cl | cis/trans | | |
| O | 3-F | H | H | Cl | Cl | cis/trans | | |
| O | 2-Cl | H | H | Cl | Cl | cis/trans | | |
| O | 4-Cl | H | H | CF$_3$ | Cl | cis/trans | | oil |
| O | 4-CF$_3$ | H | H | CF$_3$ | Cl | cis/trans | | |
| O | 3-SO$_2$CH$_3$ | H | H | CF$_3$ | Cl | cis/trans | | |
| O | 4-F | H | H | CF$_3$ | Cl | cis/trans | | oil |
| O | 3-F | H | H | CF$_3$ | Cl | cis/trans | | oil |
| O | 2-F | H | H | CF$_3$ | Cl | cis/trans | | oil |
| O | H | H | H | Br | Br | cis/trans | | |
| O | 4-F | H | H | Br | Br | cis/trans | | |
| O | 4-Cl | H | H | Br | Br | cis/trans | | |
| O | 4-Br | H | H | Br | Br | cis/trans | | |
| O | 4-SCH$_3$ | H | H | Br | Br | cis/trans | | |
| O | 4-CH$_3$ | H | H | Br | Br | cis/trans | | |
| O | H | H | 4-F | Cl | Cl | cis/trans | | |

TABLE 1-continued

| X | $R_1{}^a$ | $R_1{}^b$ | $R_2$ | $R_3$ | $R_4$ | Cyclopropane Geometry | Dia.* | Phys. Prop. |
|---|---|---|---|---|---|---|---|---|
| O | H | H | 5-F | $CF_3$ | Cl | cis/trans | | |
| O | H | H | 3-Cl | $CF_3$ | Cl | cis/trans | | |
| O | H | H | H | $CO_2CH_3$ | Cl | cis/trans | | |
| O | 4-Cl | H | H | $CO_2CH_3$ | Cl | cis/trans | | |
| O | 4-$CH_3$ | H | H | $CO_2CH_3$ | Cl | cis/trans | | |
| O | 4-F | H | H | $CO_2C_2H_5$ | Cl | cis/trans | | |
| O | H | H | H | $CO_2C_2H_5$ | Cl | cis/trans | | |
| O | H | H | H | $CH_3$ | $CH_3$ | cis/trans | | |
| O | 4-$SCH_3$ | H | H | $CH_3$ | $CH_3$ | cis/trans | | |
| O | 4-O-n-$C_4H_9$ | H | H | Cl | Cl | cis/trans | | |
| O | 4-$OCF_2H$ | H | H | Cl | Cl | cis/trans | | |
| O | 4-$OCF_2CF_2H$ | H | H | Cl | Cl | cis/trans | | |
| O | 4-$SCF_2H$ | H | H | Cl | Cl | cis/trans | | |
| O | 4-Cl | 3-Cl | H | $CF_3$ | Cl | cis/trans | | |
| O | 4-Cl | 2-F | H | $CF_3$ | Cl | cis/trans | | |
| O | 4-$CH_3$ | 2-Cl | H | $CF_3$ | Cl | cis/trans | | |
| O | 4-$OCH_3$ | 3-$OCH_3$ | H | $CF_3$ | Cl | cis/trans | | |
| O | 3,4-$OCH_2O$— | | H | Br | Br | cis/trans | | |
| O | 4-$OCH_2CH_2Cl$ | H | H | Br | Br | cis/trans | | |
| O | 4-$OCF_2CF_2H$ | H | H | Br | Br | cis/trans | | |
| S | H | H | H | Cl | Cl | cis/trans | | |
| S | H | H | H | $CF_3$ | Cl | cis/trans | | |
| S | H | H | H | Br | Cl | cis/trans | | |
| S | H | H | H | $CH_3$ | $CH_3$ | cis/trans | | |
| S | H | H | H | Br | Br | cis/trans | | |
| O | H | H | 5-Cl | Cl | Cl | cis/trans | | |
| O | H | H | 5-Cl | $CF_3$ | Cl | cis/trans | | |
| O | H | H | 5-F | Cl | Cl | cis/trans | | |
| O | H | H | 5-Cl | Br | Br | cis/trans | | |
| O | H | H | 5-F | Br | Br | cis/trans | | |
| O | 2-Cl | 4-F | H | $CF_3$ | Cl | cis/trans | | oil |
| O | 4-$OCH_3$ | H | H | $CF_3$ | Cl | cis/trans | | oil |
| O | 4-$SCH_3$ | H | H | $CF_3$ | Cl | cis/trans | | IR 1752 cm$^{-1}$ |
| O | 3-Cl | H | H | Cl | Cl | cis/trans | | |
| O | 3-Cl | H | H | $CF_3$ | Cl | cis/trans | | |
| O | 2-F | H | H | Cl | Cl | cis/trans | | |
| O | 4-Cl | H | H | Cl | Cl | cis | | oil |
| O | 4-F | H | H | Cl | Cl | cis | | m.p. 69° to 72° C. |
| O | 4-Br | H | H | Cl | Cl | cis | | |
| O | 4-$CF_3$ | H | H | Cl | Cl | cis | | |
| O | 4-$SCH_3$ | H | H | Cl | Cl | cis | | IR 1748 cm$^{-1}$ |
| O | 4-S-n-$C_4H_9$ | H | H | Cl | Cl | cis | | |
| O | 4-$OCH_3$ | H | H | Cl | Cl | cis | | oil |
| O | 3-F | H | H | Cl | Cl | cis | | oil |
| O | 2-Cl | H | H | Cl | Cl | cis | | IR 1745 cm$^{-1}$ |
| O | 4-Cl | H | H | $CF_3$ | Cl | cis | | |
| O | 4-$CF_3$ | H | H | $CF_3$ | Cl | cis | | |
| O | 3-$SO_2CH_3$ | H | H | $CF_3$ | Cl | cis | | |
| O | 4-F | H | H | $CF_3$ | Cl | cis | | oil |
| O | 3-F | H | H | $CF_3$ | Cl | cis | | oil |
| O | 2-F | H | H | $CF_3$ | Cl | cis | | oil |
| O | H | H | H | Br | Br | cis | | |
| O | 4-F | H | H | Br | Br | cis | | |
| O | 4-Cl | H | H | Br | Br | cis | | |
| O | 4-Br | H | H | Br | Br | cis | | |
| O | 4-$SCH_3$ | H | H | Br | Br | cis | | |
| O | 4-$CH_3$ | H | H | Br | Br | cis | | |
| O | H | H | 4-F | Cl | Cl | cis | | |
| O | H | H | 5-F | $CF_3$ | Cl | cis | | |
| O | H | H | 3-Cl | $CF_3$ | Cl | cis | | |
| O | H | H | H | $CO_2CH_3$ | Cl | cis | | |
| O | 4-Cl | H | H | $CO_2CH_3$ | Cl | cis | | |
| O | 4-$CH_3$ | H | H | $CO_2CH_3$ | Cl | cis | | |
| O | 4-F | H | H | $CO_2C_2H_5$ | Cl | cis | | |
| O | H | H | H | $CO_2C_2H_5$ | Cl | cis | | |
| O | H | H | H | $CH_3$ | $CH_3$ | cis | | |
| O | 4-$SCH_3$ | H | H | $CH_3$ | $CH_3$ | cis | | |
| O | 4-O-n-$C_4H_9$ | H | H | Cl | Cl | cis | | |
| O | 4-$OCF_2H$ | H | H | Cl | Cl | cis | | |
| O | 4-$OCF_2CF_2H$ | H | H | Cl | Cl | cis | | |
| O | 4-$SCF_2H$ | H | H | Cl | Cl | cis | | |
| O | 4-Cl | 3-Cl | H | $CF_3$ | Cl | cis | | |
| O | 4-Cl | 2-F | H | $CF_3$ | Cl | cis | | |
| O | 4-$CH_3$ | 2-Cl | H | $CF_3$ | Cl | cis | | |
| O | 4-$OCH_3$ | 3-$OCH_3$ | H | $CF_3$ | Cl | cis | | |

TABLE 1-continued

| X | $R_1^a$ | $R_1^b$ | $R_2$ | $R_3$ | $R_4$ | Cyclopropane Geometry | Dia.* | Phys. Prop. |
|---|---|---|---|---|---|---|---|---|
| O | 3,4-OCH$_2$O— | | H | Br | Br | cis | | |
| O | 4-OCH$_2$CH$_2$Cl | H | H | Br | Br | cis | | |
| O | 4-OCF$_2$CF$_2$H | H | H | Br | Br | cis | | |
| S | H | H | H | Cl | Cl | cis | | |
| S | H | H | H | CF$_3$ | Cl | cis | | |
| S | H | H | H | Br | Cl | cis | | |
| S | H | H | H | CH$_3$ | CH$_3$ | cis | | |
| S | H | H | H | Br | Br | cis | | |
| O | H | H | 5-Cl | Cl | Cl | cis | | |
| O | H | H | 5-Cl | CF$_3$ | Cl | cis | | |
| O | H | H | 5-F | Cl | Cl | cis | | |
| O | H | H | 5-Cl | Br | Br | cis | | |
| O | H | H | 5-F | Br | Br | cis | | |
| O | 2-Cl | 4-F | H | CF$_3$ | Cl | cis | | |
| O | 4-OCH$_3$ | H | H | CF$_3$ | Cl | cis | | |
| O | 4-SCH$_3$ | H | H | CF$_3$ | Cl | cis | | |
| O | 3-Cl | H | H | Cl | Cl | cis | | IR 1746 cm$^{-1}$ |
| O | 3-Cl | H | H | CF$_3$ | Cl | | | IR 1750 cm$^{-1}$ |
| O | 2-F | H | H | Cl | Cl | cis | | oil |
| O | 2-Cl | H | H | CF$_3$ | Cl | cis | | IR 1750 cm$^{-1}$ |
| O | 4-Cl | H | H | Cl | Cl | trans | | |
| O | 4-F | H | H | Cl | Cl | trans | | |
| O | 4-Br | H | H | Cl | Cl | trans | | |
| O | 4-CF$_3$ | H | H | Cl | Cl | trans | | |
| O | 4-SCH$_3$ | H | H | Cl | Cl | trans | | |
| O | 4-S—n-C$_4$H$_9$ | H | H | Cl | Cl | trans | | |
| O | 4-OCH$_3$ | H | H | Cl | Cl | trans | | |
| O | 3-F | H | H | Cl | Cl | trans | | |
| O | 2-Cl | H | H | Cl | Cl | trans | | |
| O | 4-Cl | H | H | CF$_3$ | Cl | trans | | |
| O | 4-CF$_3$ | H | H | CF$_3$ | Cl | trans | | |
| O | 3-SO$_2$CH$_3$ | H | H | CF$_3$ | Cl | trans | | |
| O | 4-F | H | H | CF$_3$ | Cl | trans | | |
| O | 3-F | H | H | CF$_3$ | Cl | trans | | |
| O | 2-F | H | H | CF$_3$ | Cl | trans | | |
| O | H | H | H | Br | Br | trans | | |
| O | 4-F | H | H | Br | Br | trans | | |
| O | 4-Cl | H | H | Br | Br | trans | | |
| O | 4-Br | H | H | Br | Br | trans | | |
| O | 4-SCH$_3$ | H | H | Br | Br | trans | | |
| O | 4-CH$_3$ | H | H | Br | Br | trans | | |
| O | H | H | 4-F | Cl | Cl | trans | | |
| O | H | H | 5-F | CF$_3$ | Cl | trans | | |
| O | H | H | 3-Cl | CF$_3$ | Cl | trans | | |
| O | H | H | H | CO$_2$CH$_3$ | Cl | trans | | |
| O | 4-Cl | H | H | CO$_2$CH$_3$ | Cl | trans | | |
| O | 4-CH$_3$ | H | H | CO$_2$CH$_3$ | Cl | trans | | |
| O | 4-F | H | H | CO$_2$C$_2$H$_5$ | Cl | trans | | |
| O | H | H | H | CO$_2$C$_2$H$_5$ | Cl | trans | | |
| O | H | H | H | CH$_3$ | CH$_3$ | trans | | |
| O | 4-SCH$_3$ | H | H | CH$_3$ | CH$_3$ | trans | | |
| O | 4-O—n-C$_4$H$_9$ | H | H | Cl | Cl | trans | | |
| O | 4-OCF$_2$H | H | H | Cl | Cl | trans | | |
| O | 4-OCF$_2$CF$_2$H | H | H | Cl | Cl | trans | | |
| O | 4-SCF$_2$H | H | H | Cl | Cl | trans | | |
| O | 4-Cl | 3-Cl | H | CF$_3$ | Cl | trans | | |
| O | 4-Cl | 2-F | H | CF$_3$ | Cl | trans | | |
| O | 4-CH | 2-Cl | H | CF$_3$ | Cl | trans | | |
| O | 4-OCH$_3$ | 3-OCH$_3$ | H | CF$_3$ | Cl | trans | | |
| O | 3,4-OCH$_2$O— | | H | Br | Br | trans | | |
| O | 4-OCH$_2$CH$_2$Cl | H | H | Br | Br | trans | | |
| O | 4-OCF$_2$CF$_2$H | H | H | Br | Br | trans | | |
| S | H | H | H | Cl | Cl | trans | | |
| S | H | H | H | CF$_3$ | Cl | trans | | |
| S | H | H | H | Br | Cl | trans | | |
| S | H | H | H | CH$_3$ | CH$_3$ | trans | | |
| S | H | H | H | Br | Br | trans | | |
| O | H | H | 5-Cl | Cl | Cl | trans | | |
| O | H | H | 5-Cl | CF$_3$ | Cl | trans | | |
| O | H | H | 5-F | Cl | Cl | trans | | |
| O | H | H | 5-Cl | Br | Br | trans | | |
| O | H | H | 5-F | Br | Br | trans | | |
| O | 2-Cl | 4-F | H | CF$_3$ | Cl | trans | | |
| O | 4-OCH$_3$ | H | H | CF$_3$ | Cl | trans | | |
| O | 4-SCH$_3$ | H | H | CF | Cl | trans | | |
| O | 3-Cl | H | H | Cl | Cl | trans | | |

TABLE 1-continued

| X | $R_1{}^a$ | $R_1{}^b$ | $R_2$ | $R_3$ | $R_4$ | Cyclopropane Geometry | Dia.* | Phys. Prop. |
|---|---|---|---|---|---|---|---|---|
| O | 3-Cl | H | H | $CF_3$ | Cl | trans | | |
| O | 2-F | H | H | Cl | Cl | trans | | |
| O | H | H | H | Cl | Cl | cis | B | oil |
| O | 4-F | H | H | Cl | Cl | cis | B | |
| O | 4-Br | H | H | Cl | Cl | cis | B | |
| O | 4-$CF_3$ | H | H | Cl | Cl | cis | B | |
| O | 4-$SCH_3$ | H | H | Cl | Cl | cis | B | |
| O | 4-S—n-$C_4H_9$ | H | H | Cl | Cl | cis | B | |
| O | 4-$OCH_3$ | H | H | Cl | Cl | cis | B | |
| O | 3-F | H | H | Cl | Cl | cis | B | |
| O | 2-Cl | H | H | Cl | Cl | cis | B | |
| O | 4-Cl | H | H | $CF_3$ | Cl | cis | B | |
| O | 4-$CF_3$ | H | H | $CF_3$ | Cl | cis | B | |
| O | 3-$SO_2CH_3$ | H | H | $CF_3$ | Cl | cis | B | |
| O | 4-F | H | H | $CF_3$ | Cl | cis | B | m.p. 71.5° to 74° C. |
| O | 3-F | H | H | $CF_3$ | Cl | cis | B | |
| O | 2-F | H | H | $CF_3$ | Cl | cis | B | |
| O | H | H | H | Br | Br | cis | B | |
| O | 4-F | H | H | Br | Br | cis | B | |
| O | 4-Cl | H | H | Br | Br | cis | B | |
| O | 4-Br | H | H | Br | Br | cis | B | |
| O | 4-$SCH_3$ | H | H | Br | Br | cis | B | |
| O | 4-$CH_3$ | H | H | Br | Br | cis | B | |
| O | H | H | 4-F | Cl | Cl | cis | B | |
| O | H | H | 5-F | $CF_3$ | Cl | cis | B | |
| O | H | H | 3-Cl | $CF_3$ | Cl | cis | B | |
| O | H | H | H | $CO_2CH_3$ | Cl | cis | B | |
| O | 4-Cl | H | H | $CO_2CH_3$ | Cl | cis | B | |
| O | 4-$CH_3$ | H | H | $CO_2CH_3$ | Cl | cis | B | |
| O | 4-F | H | H | $CO_2C_2H_5$ | Cl | cis | B | |
| O | H | H | H | $CO_2C_2H_5$ | Cl | cis | B | |
| O | H | H | H | $CH_3$ | $CH_3$ | cis | B | |
| O | 4-$SCH_3$ | H | H | $CH_3$ | $CH_3$ | cis | B | |
| O | 4-O—n-$C_4H_9$ | H | H | Cl | Cl | cis | B | |
| O | 4-$OCF_2H$ | H | H | Cl | Cl | cis | B | |
| O | 4-$OCF_2CF_2H$ | H | H | Cl | Cl | cis | B | |
| O | 4-$SCF_2H$ | H | H | Cl | Cl | cis | B | |
| O | 4-Cl | 3-Cl | H | $CF_3$ | Cl | cis | B | |
| O | 4-Cl | 2-F | H | $CF_3$ | Cl | cis | B | |
| O | 4-$CH_3$ | 2-Cl | H | $CF_3$ | Cl | cis | B | |
| O | 4-$OCH_3$ | 3-$OCH_3$ | H | $CF_3$ | Cl | cis | B | |
| O | 3,4-$OCH_2O$— | | H | Br | Br | cis | B | |
| O | 4-$OCH_2CH_2Cl$ | H | H | Br | Br | cis | B | |
| O | 4-$OCF_2CF_2H$ | H | H | Br | Br | cis | B | |
| S | H | H | H | Cl | Cl | cis | B | |
| S | H | H | H | $CF_3$ | Cl | cis | B | |
| S | H | H | H | Br | Cl | cis | B | |
| S | H | H | H | $CH_3$ | $CH_3$ | cis | B | |
| S | H | H | H | Br | Br | cis | B | |
| O | H | H | 5-Cl | Cl | Cl | cis | B | |
| O | H | H | 5-Cl | $CF_3$ | Cl | cis | B | |
| O | H | H | 5-F | Cl | Cl | cis | B | |
| O | H | H | 5-Cl | Br | Br | cis | B | oil |
| O | H | H | 5-F | Br | Br | cis | B | |
| O | 2-Cl | 4-F | H | $CF_3$ | Cl | cis | B | |
| O | 4-$OCH_3$ | H | H | $CF_3$ | Cl | cis | B | |
| O | 4-$SCH_3$ | H | H | $CF_3$ | Cl | cis | B | |
| O | 3-Cl | H | H | Cl | Cl | cis | B | |
| O | 3-Cl | H | H | $CF_3$ | Cl | cis | B | |
| O | 2-F | H | H | Cl | Cl | cis | B | |

*Dia. - B represents the diastereomer containing the (IR)-cis-α-S enantiomer.

TABLE 2

| X | $R_1{}^a$ | $R_1{}^b$ | $R_2$ | Phys. Prop. |
|---|---|---|---|---|
| O | H | H | H | |
| O | 4-Cl | H | H | |
| O | 4-F | H | H | IR 1750 cm$^{-1}$ |
| O | 4-$CH_3$ | H | H | |
| O | 4-$SCH_3$ | H | H | |
| O | 4-$OC_2H_5$ | H | H | |
| O | 2-F | H | H | |
| O | 3-F | H | H | |
| O | 4-$SCH_2CF_3$ | H | H | |
| O | 4-$OCH_2CF_3$ | H | H | |
| O | 4-$CF_3$ | H | H | |
| O | 4-$CH_2CH_2CH_2CH_2F$ | H | H | |
| O | 4-$S(O)C_2H_5$ | H | H | |
| O | 4-Cl | 2-Cl | H | |
| O | 4-F | 2-F | H | |
| O | 4-$CH_3$ | 2-Br | H | |
| O | H | H | 4-$CH_3$ | |
| O | H | H | 3-Cl | |
| O | H | H | 5-F | |

TABLE 2-continued

| X | $R_1^a$ | $R_1^b$ | $R_2$ | Phys. Prop. |
|---|---|---|---|---|
| O | H | H | 4-F | |
| S | H | H | H | |
| S | H | H | 4-F | |
| S | 4-CF$_3$ | H | H | |
| S | 4-Cl | H | H | |
| O | H | H | 5-Cl | |

TABLE 3

| X | $R_1^a$ | $R_1^b$ | $R_2$ | $R_5$ | Phys. Prop. |
|---|---|---|---|---|---|
| O | H | H | H | H | |
| O | H | H | H | Cl | |
| O | H | H | H | F | |
| O | H | H | H | CH$_3$ | |
| O | H | H | H | t-C$_4$H$_9$ | |
| O | H | H | H | CF$_3$ | |
| O | 4-Cl | H | H | H | |
| O | 4-Cl | H | H | t-C$_4$H$_9$ | |
| O | 4-F | H | H | Cl | |
| O | 4-F | H | H | C$_2$H$_5$ | |
| O | H | H | 5-F | H | |
| O | H | H | 5-F | Cl | |
| O | H | H | 5-F | t-C$_4$H$_9$ | |
| O | 4-OCH$_3$ | 3-Cl | H | t-C$_4$H$_9$ | |
| O | 4-Cl | 3-Cl | H | t-C$_4$H$_9$ | |
| S | H | H | H | F | |
| S | H | H | H | Cl | |
| S | H | H | H | H | |
| S | H | H | H | t-C$_4$H$_9$ | |
| O | H | H | 5-Cl | t-C$_4$H$_9$ | |

TABLE 4

| X | $R_1^a$ | $R_1^b$ | $R_2$ | $R_6$ | $R_7$ | Phys. Prop. |
|---|---|---|---|---|---|---|
| O | H | H | H | Br | Br | |
| O | 4-Cl | H | H | Br | Br | |
| O | 4-F | H | H | Br | Br | |
| O | 4-SCH$_3$ | H | H | Br | Br | |
| O | 4-CF$_3$ | H | H | Br | Br | |
| O | H | H | H | Cl | Cl | |
| O | 4-Cl | H | H | Cl | Cl | |
| O | 4-F | H | H | Cl | Cl | |
| O | 4-SCH$_3$ | H | H | Cl | Cl | |

TABLE 4-continued

| X | $R_1^a$ | $R_1^b$ | $R_2$ | $R_6$ | $R_7$ | Phys. Prop. |
|---|---|---|---|---|---|---|
| O | 4-CF$_3$ | H | H | Cl | Cl | |
| S | H | H | H | Br | Br | |
| S | H | H | H | Cl | Cl | |
| O | H | H | 5-Cl | Br | Br | |
| O | H | H | 5-F | Br | Br | |

TABLE 5

| X | $R_1^a$ | $R_1^b$ | $R_2$ | $R_8$ | $R_9$ | Phys. Prop. |
|---|---|---|---|---|---|---|
| O | H | H | H | OCH$_3$ | H | |
| O | H | H | H | OC$_2$H$_5$ | H | |
| O | H | H | H | O-i-C$_3$H$_7$ | H | |
| O | H | H | H | F | H | |
| O | H | H | H | Br | H | |
| O | H | H | H | CF$_3$ | H | |
| O | H | H | H | SCH$_3$ | H | |
| O | H | H | H | SC$_2$H$_5$ | H | |
| O | 4-Cl | H | H | Cl | H | |
| O | 4-Cl | H | H | OC$_2$H$_5$ | H | |
| O | 4-Cl | H | H | SC$_2$H$_5$ | H | |
| O | 4-F | H | H | Cl | H | |
| O | 4-F | H | H | CF$_3$ | H | |
| O | 4-F | H | H | Br | H | |
| O | H | H | H | Cl | 3-Cl | |
| O | H | H | H | Cl | 3-F | |
| O | H | H | 5-F | Cl | H | |
| O | H | H | 5-Cl | Cl | H | |
| S | H | H | H | Cl | H | |
| S | H | H | H | F | H | |
| S | H | H | H | Br | H | |
| S | H | H | H | CF$_3$ | H | |
| S | H | H | H | OC$_2$H$_5$ | H | |

TABLE 6

($R_1^b = $ H)

| X | $R_1^a$ | $R_2$ | m | $R_{10}$ | $R_{11}$ | $R_{12}$ | $R_{13}$ | $R_{14}$ | Phys. Prop. |
|---|---|---|---|---|---|---|---|---|---|
| O | H | H | 0 | H | H | Cl | Cl | Cl | |
| O | H | H | 0 | H | H | Cl | Cl | OCH$_3$ | |
| O | H | H | 0 | H | H | Cl | Cl | OC$_2$H$_5$ | |
| O | H | H | 0 | H | H | Cl | Cl | OCF$_2$H | |
| O | H | H | 0 | H | H | F | F | Cl | |
| O | H | H | 0 | H | H | F | F | F | |
| O | H | H | 0 | H | H | F | F | H | |
| O | H | H | 0 | H | H | F | F | OCF$_2$CF$_2$H | |
| O | H | H | 1 | F | F | F | F | Cl | |
| O | H | H | 1 | F | F | F | F | F | |
| O | H | H | 1 | F | F | F | F | OC$_2$H$_5$ | oil |
| O | H | H | 1 | F | F | F | F | OCF$_2$H | |
| O | H | H | 1 | F | F | F | F | OCF$_2$CF$_2$H | |
| O | H | H | 1 | Cl | Cl | F | F | Cl | |
| O | H | H | 1 | Cl | Cl | F | F | OC$_2$H$_5$ | |
| O | H | H | 1 | H | H | H | H | Cl | |
| O | H | H | 1 | H | H | H | H | OC$_2$H$_5$ | |
| O | 4-Cl | H | 0 | H | H | Cl | Cl | Cl | |
| O | 4-F | H | 0 | H | H | F | F | OC$_2$H$_5$ | |
| O | 4-SCH$_3$ | H | 1 | F | F | F | F | OC$_2$H$_5$ | |
| O | 4-F | H | 1 | F | F | F | F | OC$_2$H$_5$ | oil |
| O | H | 5-Cl | 1 | F | F | F | F | OC$_2$H$_5$ | |
| O | H | 5-F | 1 | F | F | F | F | OC$_2$H$_5$ | |
| S | H | H | 1 | F | F | F | F | OC$_2$H$_5$ | |

TABLE 7

R=R—A

| X | $R_1^a$ | $R_3$ | $R_4$ | Phys. Prop. |
|---|---|---|---|---|
| O | 4-F | Cl | Cl | |
| O | 4-F | CF$_3$ | Cl | |
| O | 4-Cl | Cl | Cl | |
| O | 4-Cl | CF$_3$ | Cl | |
| S | H | Cl | Cl | |
| S | H | CF$_3$ | Cl | |
| O | H | Br | Br | |

TABLE 7-continued

| | | | | |
|---|---|---|---|---|
| O | 4-F | Br | Br | |
| O | H | $CO_2CH_3$ | Cl | |
| O | 4-F | $CO_2CH_3$ | Cl | |
| O | H | $CH_3$ | $CH_3$ | |
| O | H | $CF_3$ | Cl | oil |

R=R—B

| X | $R_1{}^a$ |
|---|---|
| O | H |
| O | 4-F |
| O | 4-Cl |
| O | $4-OCH_3$ |
| S | H |
| S | 4-F |

TABLE 8

R=R—A

| X | $R_1{}^a$ | $R_3$ | $R_4$ | Phys. Prop. |
|---|---|---|---|---|
| O | 4-F | Cl | Cl | |
| O | 4-F | $CF_3$ | Cl | |
| O | 4-Cl | Cl | Cl | |
| O | 4-Cl | $CF_3$ | Cl | |
| S | H | Cl | Cl | |
| S | H | $CF_3$ | Cl | |
| O | H | Br | Br | |
| O | 4-F | Br | Br | |
| O | H | $CO_2CH_3$ | Cl | |
| O | 4-F | $CO_2CH_3$ | Cl | |
| O | H | $CH_3$ | $CH_3$ | |
| O | H | Cl | Cl | oil |

R=R—B

| X | $R_1{}^a$ |
|---|---|
| O | H |
| O | 4-F |
| O | 4-Cl |
| O | $4-OCH_3$ |
| S | H |
| S | 4-F |

TABLE 9

R=R—A

| X | $R_1{}^a$ | $R_3$ | $R_4$ | Phys. Prop. |
|---|---|---|---|---|
| O | 4-F | Cl | Cl | |
| O | 4-F | $CF_3$ | Cl | |
| O | 4-Cl | Cl | Cl | |
| O | 4-Cl | $CF_3$ | Cl | |
| S | H | Cl | Cl | |
| S | H | $CF_3$ | Cl | |
| O | H | Br | Br | |
| O | 4-F | Br | Br | |
| O | H | $CO_2CH_3$ | Cl | |
| O | 4-F | $CO_2CH_3$ | Cl | |
| O | H | $CH_3$ | $CH_3$ | |
| O | H | Cl | Cl | oil |

R=R—B

| X | $R_1{}^a$ |
|---|---|
| O | H |
| O | 4-F |
| O | 4-Cl |
| O | $4-OCH_3$ |
| S | H |
| S | 4-F |

TABLE 10

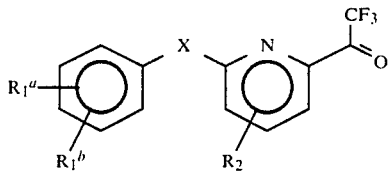

| X | $R_1{}^a$ | $R_1{}^b$ | $R_2$ | Phys. Prop. |
|---|---|---|---|---|
| O | 4-Cl | H | H | IR 1740 cm$^{-1}$ |
| O | 4-F | H | H | IR 1740 cm$^{-1}$ |
| O | 4-Br | H | H | |
| O | $4-CF_3$ | H | H | |
| O | $4-OCH_3$ | H | H | oil |
| O | $4-SCH_3$ | H | H | IR 1740 cm$^{-1}$ |
| O | $4-SO_2CH_3$ | H | H | |
| O | $4-OCF_2H$ | H | H | |
| O | 2-F | 4-F | H | |
| O | 2-Cl | 4-Cl | H | |
| O | 3,4-$OCH_2O$— | | H | |
| O | H | H | $3-CH_3$ | |
| O | H | H | 4-F | |
| O | H | H | 5-F | |
| S | H | H | H | m.p. 76° to 78° C. |
| S | 4-Cl | H | H | |
| S | 4-F | H | H | |
| S | $4-CF_3$ | H | H | |
| O | H | H | 5-Cl | |
| O | H | H | $5-CH_3$ | |
| O | H | H | 5-Br | |
| O | H | H | $5-CF_3$ | |
| O | 3-F | H | H | oil |
| O | 3-Cl | H | H | IR 1735 cm$^{-1}$ |
| O | 2-Cl | 4-F | H | IR 1745 cm$^{-1}$ |
| O | 2-F | H | H | oil |
| O | 2-Cl | H | H | oil |

TABLE 11

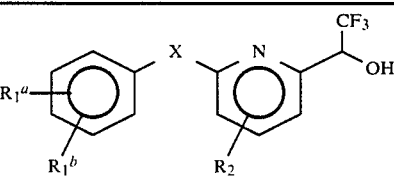

| X | $R_1{}^a$ | $R_1{}^b$ | $R_2$ | Phys. Prop. |
|---|---|---|---|---|
| O | 4-Cl | H | H | m.p. 69° to 71° C. |
| O | 4-F | H | H | m.p. 42° to 44° C. |
| O | 4-Br | H | H | |
| O | $4-CF_3$ | H | H | |
| O | $4-OCH_3$ | H | H | m.p. 98° to 101° C. |
| O | $4-SCH_3$ | H | H | m.p. 79° to 81° C. |
| O | $4-SO_2CH_3$ | H | H | |
| O | $4-OCF_2H$ | H | H | |
| O | 2-F | 4-F | H | |
| O | 2-Cl | 4-Cl | H | |
| O | 3,4-$OCH_2O$— | | H | |
| O | H | H | $3-CH_3$ | |
| O | H | H | 4-F | |
| O | H | H | 5-F | |
| S | H | H | H | m.p. 79° to 80.5° C. |
| S | 4-Cl | H | H | |
| S | 4-F | H | H | |
| S | $4-CF_3$ | H | H | |
| O | H | H | 5-Cl | |
| O | H | H | $5-CH_3$ | |
| O | H | H | 5-Br | |
| O | H | H | $5-CF_3$ | |
| O | 3-F | H | H | oil |
| O | 3-Cl | H | H | m.p. 85° to 87° C. |
| O | 2-Cl | 4-F | H | oil |
| O | 2-F | H | H | oil |

TABLE 11-continued

[Structure: R₁ᵃ and R₁ᵇ substituted phenyl connected via X to a pyridine ring with R₂ substituent and CF₃-CH(OH) group]

| X | R₁ᵃ | R₁ᵇ | R₂ | Phys. Prop. |
|---|-----|-----|-----|-------------|
| O | 2-Cl | H | H | oil |

UTILITY

The compounds of the present invention exhibit activity against a wide spectrum of foliar and soil inhabiting insects and mites. Some of the compounds of the invention surprisingly retain activity in the soil. Those skilled in the art will recognize that not all compounds are equally effective against all insects or mites, but compounds of this invention display control of many of the economically important pest species of the insect orders Lepidoptera, Homoptera, and Coleoptera among many others as well as important mite species of the order Acari. The specific species, for which control is exemplified below, are: fall armyworm, *Spodoptera frugiperda*; tobacco budworm, *Heliothis virescens*; boll weevil, *Anthonomus grandis*; European corn borer, *Ostrinia nubilalis*; southern corn rootworm, *Diabrotica undecimpunctata howardi*; ester leafhopper, *Macrosteles fascifrons*; black bean aphid, *Aphis fabae*; and the two-spotted spider mite *Tetranychus urticae*. The pest control afforded by the compounds of the present invention is not limited, however, to these species.

FORMULATION AND USE

The compounds of this invention will generally be used in formulation with a liquid or solid diluent or with an organic solvent carrier. Useful formulations of the compounds of Formula I can be prepared in conventional ways. They include dusts, granules, pellets, solutions, suspensions, emulsions, wettable powders, emulsifiable concentrates, dry flowables and the like. Many of these may be applied directly. Sprayable formulations can be extended in suitable media and used at spray volumes of from about one to several hundred liters per hectare. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following approximate proportions:

|  | Active Ingredient | Percent by Weight Diluent(s) | Surfactant(s) |
|---|---|---|---|
| Wettable Powders | 25–90 | 0–74 | 1–10 |
| Oil Suspensions, Emulsions, Solutions, (including Emulsifiable Concentrates) | 5–50 | 40–95 | 0–15 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, New Jersey. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pages 147 and following, and "Perry's Chemical Engineer's Handbook", 4th Ed., McGraw-Hill, New York, 1963, pages 8 to 59 and following.

Examples of useful formulations of compounds of the present invention are as follows:

EXAMPLE 17

Emulsifiable Concentrate

| | |
|---|---|
| cis-[1-(6-phenoxy-2-pyridinyl) -2,2,2-trifluoroethyl] 3-(2,2-dichloroethenyl)-2,2-dimethylcyclopropane carboxylate | 30% |
| blend of oil soluble sulfonates and polyoxyethylene ethers | 4% |
| xylene | 66% |

The ingredients are combined and stirred with gentle warming to speed solution. A fine screen filter is included in packaging operation to insure the absence of any extraneous undissolved material in the product.

EXAMPLE 18

Wettable Powder

| | |
|---|---|
| [1-(6-phenoxy-2-pyridinyl)-2,2,2-trifluoroethyl] 3-(2-chloro-3,3,3-trifluoro-1-propenyl)-2,2-dimethylcyclopropanecarboxylate | 30% |
| sodium alkylnaphthalenesulfonate | 2% |
| sodium ligninsulfonate | 2% |
| synthetic amorphous silica | 3% |
| kaolinite | 63% |

The active ingredient, warmed to reduce viscosity, is sprayed onto the inert materials in a blender. After grinding in a hammer-mill, the material is reblended and sifted through a 50 mesh screen.

EXAMPLE 19

Dust

| Wettable powder of Example 18 | 10% |
|---|---|
| pyrophyllite (powder) | 90% |

The wettable powder and the pyrophyllite diluent are thoroughly blended and then packaged. The product is suitable for use as a dust.

EXAMPLE 20

Granule

| [1-(6-phenoxy-2-pyridinyl)-2,2,2-trifluoroethyl] 4-chloro-α-(1-methylethyl)benzeneacetate | 10% |
|---|---|
| attapulgite granules (low volative matter, 0.71/0.30 mm; U.S.S. No. 25–50 sieves) | 90% |

The active ingredient is warmed to reduce viscosity and sprayed upon dedusted and pre-warmed attapulgite granules in a double cone blender. The granules are then allowed to cool and are packaged.

EXAMPLE 21

Granule

| Wettable powder of Example 18 | 15% |
|---|---|
| gypsum | 69% |
| potassium sulfate | 16% |

The ingredients are blended in a rotating mixer and water sprayed on to accomplish granulation. When most of the material has reached the desired range of 0.1 to 0.42 mm (U.S.S. No. 18 to 40 sieves), the granules are removed, dried, and screened. Oversize material is crushed to produce additional material in the desired range. These granules contain 4.5% active ingredient.

EXAMPLE 22

Solution

| cis-[1-(6-phenoxy-2-pyridinyl)-2,2,2-trifluoroethyl] 3-(2,2-dichloroethenyl)-2,2-dimethylcyclopropane carboxylate | 50% |
|---|---|
| isophorone | 50% |

The ingredients are combined and stirred to produce a solution suitable for direct, low volume application.

Compounds of Formula I can also be mixed with one or more other insecticides, fungicides, nematocides, bactericides, acaricides, or other biologically active compounds to form a multi-component pesticide giving an even broader spectrum of effective agricultural protection. In particular, it may be advantageous to combine a compound of Formula I with substances that have a synergistic or potentiating action. Typical substances are the pyrethrin synergists of which the following are examples: [2-(2-butoxyethoxy)ethoxy]-4,5-methylenedioxy-2-propyltoluene (piperonyl butoxide), 3-hexyl-5-(3,4-methylenedioxyphenyl)-2-cyclohexanone cyclohexanone (piperonyl cyclonene), 2-(3,4-methylenedioxyphenoxy)-3,6,9-trioxaundecane, 1,2-(methylenedioxy)-4-[2-(octylsulfinyl)propyl]benzene, dipropyl-5,6,7,8-tetrahydro-7-methylnaphtho-[2,3-d]-3-dioxole-5,6-dicarboxylate, as well as propynyl ethers and propynyl oximes. Examples of other agricultural protectants with which compounds of the present invention can be mixed or formulated are:

Insecticides:
3-hydroxy-N-methylcrotonamide(dimethylphosphate)ester (monocrotophos)
methylcarbamic acid, ester with 2,3-dihydro-2,2-dimethyl-7-benzofuranol (carbofuran)
O-[2,4,5-trichloro-α-(chloromethyl)benzyl]phosphoric acid, O',O'-dimethyl ester (tetrachlorvinphos)
2-mercaptosuccinic acid, diethyl ester, S-ester with thionophosphoric acid, dimethyl ester (malathion)
phosphorothioic acid, O,O-dimethyl, O-p-nitrophenyl ester (methyl parathion)
methylcarbamic acid, ester with α-naphthol (carbaryl)
methyl O-(methylcarbamoyl)thiolacetohydroxamate (methomyl)
N'-(4-chloro-o-tolyl)-N,N-dimethylformamidine (chlordimeform)
O,O-diethyl-O-(2-isopropyl-4-methyl-6-pyrimidylphosphorothioate (diazinon)
octachlorocamphene (toxaphene)
O-ethyl O-p-nitrophenyl phenylphosphonothioate (EPN)
(S)-α-cyano-m-phenoxybenzyl(1R,3R)-3-(2,2-dibromovinyl)-2,2-dimethylcyclopropanecarboxylate (deltamethrin)
Methyl N',N'-dimethyl-N-[(methylcarbamoyl)oxy]-1-thiooxamimidate (oxamyl)
cyano(3-phenoxyphenyl)-methyl-4-chloro-α-(1-methylethyl)benzeneacetate (fenvalerate)
(3-phenoxyphenyl)methyl(±)-cis,trans-3-(2,2-dichloroethenyl)-2,2-dimethylcyclopropanecarboxylate (permethrin)
α-cyano-3-pheonxybenzyl 3-(2,2-dichlorovinyl)-2,2-dimethylcyclopropane carboxylate (cypermethrin)
O-ethyl-S-(p-chlorophenyl)ethylphosphonodithioate (profenofos)
phosphorothiolothionic acid, O-ethyl-O-[4-(methylthio)phenyl]-S-n-propyl ester (sulprofos).

Additional insecticides are listed hereafter by their common names: triflumuron, diflubenzuron, methoprene, buprofezin, thiodicarb, acephate, azinphos-methyl, chlorpyrifos, dimethoate, fonophos, isofenphos, methidathion, methamidiphos, monocrotophos, phosmet, phosphamidon, phosalone, pirimicarb, phorate, profenofos, terbufos, trichlorfon, methoxychlor, bifenthrin, biphenate, cyfluthrin, fenpropathrin, fluvalinate, flucythrinate, tralomethrin, metaldehyde and rotenone.

Fungicides:
methyl 2-benzimidazolecarbamate (carbendazim)
tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
1-[2-(2,4-dichlorphenyl)-4-propyl-1,3-dioxolan-2-ylmethyl]-1H-1,2,4-triazole (propiconazole)
2-cyano-N-ethylcarbamoyl-2-methoxyiminoactamide (cymoxanil)

1-(4-chlorophenoxy)-3,3-dimethyl-1-(1H-1,2,4-triazol-1-yl)-2-butanone (triadimefon)
N-(trichloromethylthio)tetrahydrophthalimide (captan)
N-(trichloromethylthio)phthalimide (folpet)
1-[[[bis(4-fluorophenyl)][methyl]silyl]methyl]-1H-1,2,4-triazole.

Nematocides:
S-methyl 1-(dimethylcarbamoyl)-N-(methylcarbamoyloxy)thioformimidate
S-methyl 1-carbamoyl-N-(methylcarbamoyloxy)thioformimidate
N-isopropylphosphoramidic acid, O-ethyl O'-[4-(methylthio)-m-tolyl]diester (fenamiphos).

Bactericides:
tribasic copper sulfate
streptomycin sulfate.

Acaricides:
senecioic acid, ester with 2-sec-butyl-4,6-dinitrophenol (binapacryl)
6-methyl-1,3-dithiolo[4,5-β]quinoxalin-2-one (oxythioquinox)
ethyl 4,4'-dichlorobenzilate (chlorobenzilate)
1,1-bis(p-clorophenyl)-2,2,2-trichloroethanol (dicofol)
bis(pentachloro-2,4-cyclopentadien-1-yl) (dienochlor)
tricyclohexyltin hydroxide (cyhexatin)
trans-5-(4-chlorophenyl)-N-cyclohexyl-4-methyl-2-oxothiazolidine-3-carboxamide (hexythiazox)
amitraz
propargite
fenbutatin-oxide
bisclofentezin.

Biological:
Bacillus thuringiensis
Avermectin B.

APPLICATION

Insects and mites are controlled and agricultural crops are protected by applying one or more of the Formula I compounds of this invention, in an effective amount, to the locus of infestation, to the area to be protected, or directly on the pests to be controlled. A preferred method of application is by spraying with spray equipment that distributes the compound on the foliage, in the soil, or to the plant part that is infested or needs to be protected. Alternatively, granular formulations of these compounds can be applied to soil or foliage or, optionally, incorporated into the soil. Either aerial or ground application can be used.

The phenoxypyridinyl compound(s) of this invention can be applied in its(their) pure state, but most often application will be of a formulation comprising one or more compounds of this invention, in an agriculturally suitable carrier or diluent. A most preferred method of application involves spraying a water dispersion or refined oil solution of the compounds.

The rate of application of the Formula I compounds required for effective control will depend on such factors as the species of insect or mite to be controlled, the pest's life stage, its size, its location, the host crop, time of year of application, ambient moisture, temperature conditions, and the like. In general, application rates of 0.05 to 2 kg of active ingredient per hectare are sufficient to provide effective control in large scale field operations under normal circumstances, but as little as 0.01 kg/hectare may be sufficient or as much as 8 kg/hectare may be required, depending upon the factors listed above.

The following Examples demonstrate the control efficacy of compounds of Formula I on specific insect and mite pests wherein Compounds 1 through 14 are the compounds of Examples 1 through 14 and the remaining compounds are those identified in Table 12.

TABLE 12

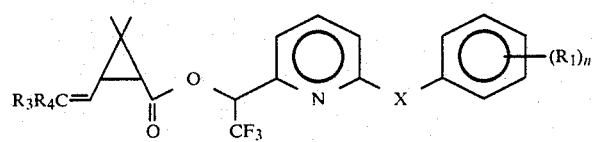

| Compound | $(R_1)_n$ | $R_3$ | $R_4$ | X | Cyclopropane isomer composition cis/trans |
|---|---|---|---|---|---|
| 17 | 4-OMe | Cl | Cl | O | 100/0 |
| 18 | 4-OMe | $CF_3$ | Cl | O | 30/70 |
| 19 | 4-SMe | Cl | Cl | O | 100/0 |
| 20 | 4-SMe | $CF_3$ | Cl | O | 30/70 |
| 21 | 4-F | $CF_3$ | Cl | O | 40/60 |
| 22 | 4-F | $CF_3$ | Cl | O | 100/0 |
| 23 | 4-Cl | Cl | Cl | O | 100/0 |
| 24 | 4-Cl | $CF_3$ | Cl | O | 40/60 |
| 25 | 3-F | Cl | Cl | O | 100/0 |
| 26 | 3-F | $CF_3$ | Cl | O | 30/70 |
| 27 | 3-Cl | Cl | Cl | O | 100/0 |
| 28 | 3-Cl | $CF_3$ | Cl | O | 100/0 |
| 29 | 2-F | Cl | Cl | O | 100/0 |
| 30 | 2-F | $CF_3$ | Cl | O | 30/70 |
| 31 | 2-Cl | Cl | Cl | O | 100/0 |
| 32 | 2-Cl | $CF_3$ | Cl | O | 100/0 |
| 33 | 2-Cl,4-F | $CF_3$ | Cl | O | 30/70 |
| 34 | H | Cl | Cl | S | 100/0 |
| 35 | H | $CF_3$ | Cl | S | 30/70 |
| 36(A)* | H | Cl | Cl | O | 100/0 |
| 36(B)* | H | Cl | Cl | O | 100/0 |
| 37(A)* | H | $CF_3$ | Cl | O | 100/0 |

TABLE 12-continued

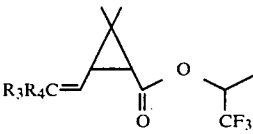

| Compound | $(R_1)_n$ | $R_3$ | $R_4$ | X | Cyclopropane isomer composition cis/trans |
|---|---|---|---|---|---|
| 37(B)* | H | $CF_3$ | Cl | O | 100/0 |
| 38 | | | | | |

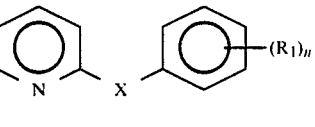

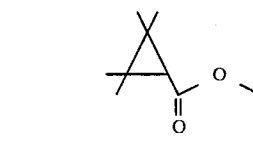

| 39 | H |
| 40 | 4-F |

*A is assigned the (1R)—cis-α-R/(1S)—cis-α-S configuration
B is assigned the (1R)—cis-α-S/(1S)—cis-α-R configuration

EXAMPLE 23

Fall Armyworm

Test units, each consisting of an 8-ounce plastic cup containing a layer of wheat germ diet, approximately 0.5 cm thick, were prepared. Ten third-instar larvae of fall armyworm (*Spodoptera frugiperda*) were placed into each cup. Solutions of each of the below-listed test compounds (acetone/distilled water 75/25 solvent) were sprayed onto the cups, a single solution per cup. Spraying was accomplished by passing the cups, on a conveyer belt, directly beneath a flat fan hydraulic nozzle which discharged the spray at a rate of 0.5 pounds of active ingredient per acre (about 0.55 kg/ha) at 30 p.s.i. The cups were then covered and held at 27° C. and 50% relatively humidity for 72 hours, after which time mortality readings were taken. The results are tabulated below.

| Compound | % Mortality 72 hours post-treatment |
|---|---|
| 1 | 100 |
| 2 | 100 |
| 3 | 100 |
| 4 | 100 |
| 5 A | 90 |
| 5 B | 100 |
| 6 A | 100 |
| 6 B | 100 |
| 7 B | 100 |
| 8 | 100 |
| 9 | 100 |
| 10 A | 27 |
| 10 B | 100 |
| 11 | 100 |
| 12 | 100 |
| 13 | 100 |
| 17 | 100 |
| 18 | 100 |
| 19 | 47 |
| 20 | 97 |
| 21 | 100 |
| 22 | 100 |
| 23 | 100 |
| 24 | 100 |
| 25 | 100 |
| 26 | 100 |
| 27 | 100 |
| 28 | 100 |
| 29 | 100 |
| 30 | 100 |
| 31 | 97 |
| 32 | 100 |
| 33 | 65 |
| 34 | 100 |
| 35 | 100 |
| 36 A | 87 |
| 36 B | 100 |
| 37 A | 7 |
| 37 B | 100 |
| 38 | 100 |
| 39 | 97 |
| 40 | 100 |

EXAMPLE 24

Tobacco Budworm

The test procedure of Example 23 was repeated for efficacy against third-instar larvae of the tobacco budworm (*Heliothis virescens*). The results are tabulated below.

| Compound | % Mortality 48 hours post-treatment |
|---|---|
| 1 | 100 |
| 2 | 100 |
| 3 | 100 |
| 4 | 100 |
| 5 A | 80 |
| 5 B | 100 |
| 6 A | 97 |
| 6 B | 97 |
| 7 B | 100 |
| 8 | 100 |
| 9 | 100 |
| 10 A | 33 |
| 10 B | 100 |
| 11 | 100 |
| 12 | 100 |
| 13 | 100 |
| 17 | 97 |
| 18 | 100 |
| 19 | 87 |
| 20 | 100 |
| 21 | 100 |
| 22 | 100 |
| 23 | 100 |
| 24 | 100 |
| 25 | 100 |
| 26 | 100 |
| 27 | 100 |
| 28 | 100 |
| 29 | 100 |
| 30 | 100 |
| 31 | 100 |
| 32 | 100 |
| 33 | 67 |
| 34 | 97 |
| 35 | 93 |
| 36 A | 50 |
| 36 B | 100 |
| 37 A | 3 |
| 37 B | 100 |
| 38 | 100 |
| 39 | 93 |
| 40 | 87 |

EXAMPLE 25

European Corn Borer

Test units, each consisting of an 8-ounce plastic cup containing a one-inch square of wheat germ/soyflour diet were prepared. Five third-instar larvae of the European corn borer (*Ostrinia nubilali*) were placed into each cup. The test units were sprayed as described in Example 23 with individual solutions of the below-listed compounds. The cups were then covered and held at 27° C. and 50% relative humidity for 48 hours, after which time mortality readings were taken. The results are tabulated below.

| Compound | % Mortality 48 hours post-treatment |
|---|---|
| 1 | 100 |
| 2 | 87 |
| 3 | 100 |
| 4 | 100 |
| 5 A | 13 |
| 5 B | 100 |
| 6 A | 90 |
| 6 B | 100 |
| 7 B | 100 |
| 8 | 93 |
| 9 | 100 |
| 10 A | 0 |
| 10 B | 100 |
| 11 | 100 |
| 12 | 100 |
| 13 | 100 |
| 17 | 100 |
| 18 | 100 |
| 19 | 53 |
| 20 | 67 |
| 21 | 100 |
| 22 | 100 |
| 23 | 93 |
| 24 | 90 |
| 25 | 100 |
| 26 | 100 |
| 27 | 100 |
| 28 | 100 |
| 29 | 100 |
| 30 | 100 |
| 31 | 67 |
| 32 | 100 |
| 33 | 65 |
| 34 | 100 |
| 35 | 93 |
| 36 A | 33 |
| 36 B | 100 |
| 37 A | 7 |
| 37 B | 100 |
| 38 | 100 |
| 39 | 53 |
| 40 | 87 |

EXAMPLE 26

Southern Corn Rootworm

Test units, each consisting of an 8-ounce plastic cup containing 1 sprouted corn seed, were prepared. The test units were sprayed as described in Example 23 with individual solutions of the below-listed compounds. After the spray on the cups had dried, five third-instar larvae of the southern corn rootworm (*Diabrotica undecimpunctata howardi*) were placed into each cup. A moistened dental wick was inserted into each cup to prevent drying and the cups were then covered. The cups were then held at 27° C. and 50% relative humidity for 48 hours, after which time mortality readings were taken. The results are tabulated below.

| Compound | % Mortality 48 hours post-treatment |
|---|---|
| 1 | 100 |
| 2 | 60 |
| 3 | 100 |
| 4 | 100 |
| 5 A | 100 |
| 5 B | 100 |
| 6 A | 100 |
| 6 B | 100 |
| 7 B | 100 |
| 8 | 100 |
| 9 | 100 |
| 10 A | 7 |
| 10 B | 100 |
| 11 | 100 |
| 12 | 100 |
| 13 | 100 |
| 17 | 100 |
| 18 | 100 |
| 19 | 100 |
| 20 | 100 |
| 21 | 100 |
| 22 | 100 |
| 23 | 100 |
| 24 | 100 |
| 25 | 100 |
| 26 | 100 |

-continued

| Compound | % Mortality 48 hours post-treatment |
|---|---|
| 27 | 87 |
| 28 | 87 |
| 29 | 100 |
| 30 | 100 |
| 31 | 80 |
| 32 | 47 |
| 33 | 67 |
| 34 | 100 |
| 35 | 100 |
| 36 A | 100 |
| 36 B | 100 |
| 37 A | — |
| 37 B | 100 |
| 38 | 100 |
| 39 | 100 |
| 40 | 93 |

EXAMPLE 27

Boll Weevil

Five adult boll weevils (*Anthonomus grandis*) were placed into each of a series of 9-ounce cups. The test procedure employed was then otherwise the same as in Example 23. Mortality readings taken 48 hours after treatment are tabulated below.

| Compound | % Mortality 48 hours post-treatment |
|---|---|
| 1 | 100 |
| 2 | 100 |
| 3 | 100 |
| 4 | 100 |
| 5 A | 47 |
| 5 B | 100 |
| 6 A | 47 |
| 6 B | 100 |
| 7 B | 100 |
| 8 | 100 |
| 9 | 100 |
| 10 A | 20 |
| 10 B | 93 |
| 11 | 100 |
| 12 | 100 |
| 13 | 73 |
| 17 | 100 |
| 18 | 100 |
| 19 | 100 |
| 20 | 100 |
| 21 | 100 |
| 22 | 100 |
| 23 | 100 |
| 24 | 100 |
| 25 | 100 |
| 26 | 100 |
| 27 | 60 |
| 28 | 73 |
| 29 | 100 |
| 30 | 100 |
| 31 | 47 |
| 32 | 100 |
| 33 | — |
| 34 | 100 |
| 35 | 100 |
| 36 A | 73 |
| 36 B | 100 |
| 37 A | 0 |
| 37 B | 100 |
| 38 | 100 |
| 39 | 100 |
| 40 | 47 |

EXAMPLE 28

Black Bean Aphid

Test units consisting of a single nasturtium (Tropaeolum sp.) leaf infested with 5 to 10 black bean aphids (*Aphis fabae*) were prepared. Each leaf was cut and individually held in a 1-dram glass vial filled with a 10% sugar solution prior to and after spraying. During spraying, the infested leaves were inverted to expose the aphids, and each leaf was held in place by a clip. Leaves were sprayed with individual solutions of the below-listed compounds following the spray procedure of Example 23. Sprayed leaves were returned to the individual glass vials, covered with a clear plastic 1-ounce cup and were held at 27° C. and 50% relative humidity for 48 hours, after which time mortality readings were taken. The results are tabulated below.

| Compound | % Mortality 48 hours post-treatment |
|---|---|
| 1 | 100 |
| 2 | 100 |
| 3 | 100 |
| 4 | 100 |
| 5 A | 91 |
| 5 B | 100 |
| 6 A | 100 |
| 6 B | 100 |
| 7 B | 100 |
| 8 | 100 |
| 9 | 100 |
| 10 A | 100 |
| 10 B | 100 |
| 11 | 100 |
| 12 | 100 |
| 13 | 100 |
| 17 | 100 |
| 18 | 100 |
| 19 | 100 |
| 20 | 87 |
| 21 | 98 |
| 22 | 100 |
| 23 | 100 |
| 24 | 100 |
| 25 | 100 |
| 26 | 100 |
| 27 | 100 |
| 28 | 100 |
| 29 | 100 |
| 31 | 99 |
| 32 | 100 |
| 33 | 93 |
| 34 | 100 |
| 35 | 96 |
| 36 A | 100 |
| 36 B | 100 |
| 37 A | 100 |
| 37 B | 100 |
| 38 | 100 |
| 39 | 90 |
| 40 | 90 |

EXAMPLE 29

Aster Leafhopper

Test units were prepared from a series of 12-ounce cups, each containing oat (*Avena sativa*) seedlings in a 1-inch layer of sterilized soil. The test units were sprayed as described in Example 23 with individual solutions of the below-listed compounds. After the oats had dried from the spraying, between 10 and 15 adult aster leafhoppers (*Mascrosteles fascifrons*) were aspirated into each of the covered cups. The cups were held at 27° C. and 50% relative humidity for 48 hours, after which time mortality readings were taken. The results are tabulated below.

| Compound | % Mortality 48 hours post-treatment |
|---|---|
| 1 | 100 |
| 3 | 100 |
| 4 | 100 |
| 5 A | 100 |
| 5 B | 100 |
| 6 A | 100 |
| 6 B | 100 |
| 7 B | 100 |
| 8 | 100 |
| 9 | 100 |
| 10 A | 52 |
| 10 B | 100 |
| 11 | 100 |
| 12 | 100 |
| 13 | 100 |
| 17 | 100 |
| 18 | 100 |
| 19 | 85 |
| 20 | 79 |
| 21 | 100 |
| 22 | 100 |
| 23 | 100 |
| 24 | 100 |
| 25 | 100 |
| 26 | 100 |
| 27 | 100 |
| 28 | 100 |
| 29 | 100 |
| 30 | 100 |
| 31 | 100 |
| 32 | 100 |
| 33 | 100 |
| 34 | 100 |
| 35 | 100 |
| 36 A | 100 |
| 36 B | 100 |
| 37 A | 17 |
| 37 B | 100 |
| 38 | 100 |
| 39 | 4 |
| 40 | 60 |

EXAMPLE 30

Soil Control of Southern Corn Rootworm

Test units, each consisting of a three-inch cylindrical pot containing 200 grams of moist sassafras loam soil and 2 kernels of Dekalb T1100 corn were prepared. Spraying was accomplished by passing the pots, on a conveyor belt, directly beneath a flat fan hydraulic nozzle which discharged the spray at a rate of 0.25 pounds of active ingredient per acre (about 0.275 kg/ha) at 30 p.s.i. After the test units had been sprayed, the corn seed was covered with soil and ten third-instar southern corn rootworm larvae (*Diabrotica undecimpunctata howardi*) were added to each unit. Test units were held at 24° C., 70% relative humidity and under a photo cycle of 16 hours of light/8 hours of darkness for 7 days, after which time control readings were taken. Control was measured by root injury ratings of 1 to 5, where 1 was no injury and 5 was complete destruction of the root system. Percent of corn seedlings that emerged also was utilized to measure control. No plant injury was observed. The results are tabulated below.

| Compound | Root injury rating | % Seedling Emergence |
|---|---|---|
| 1 | 1.4 | 100 |
| 3 | 1.9 | 88 |
| 4 | 1.0 | 100 |
| 5 B | 1.0 | 100 |
| 6 A | 3.3 | 38 |
| 6 B | 1.1 | 100 |
| 8 | 1.3 | 88 |
| 9 | 1.5 | 88 |
| 10 B | 1.4 | 100 |
| 11 | 2.1 | 75 |
| 12 | 2.6 | 38 |
| 13 | 1.3 | 88 |
| 18 | 2.8 | 50 |
| 19 | 3.5 | 13 |
| 20 | 3.5 | 0 |
| 21 | 1.6 | 100 |
| 22 | 2.1 | 75 |
| 23 | 1.9 | 100 |
| 24 | 2.3 | 75 |
| 25 | 1.6 | 88 |
| 26 | 1.3 | 100 |
| 30 | 1.9 | 75 |
| 35 | 3.8 | 0 |
| 36 B | 2.8 | 88 |
| 37 B | 1.3 | 100 |
| 38 | 1.3 | 100 |

EXAMPLE 31

Two-Spotted Spider Mite

Test units, each consisting of one-inch square sections of kidney bean leaves were infested with 20 to 30 adult two-spotted spider mites (*Tetranychus urticae*) and sprayed as described in Example 23 with individual solutions of the below-listed compounds. Sprayed leaf sections were then placed on a layer of moistened cotton in a Petri dish and held at 27° C. and 50% relative humidity for 48 hours, after which time mortality readings were taken. The results are tabulated below.

| Compound | % Mortality 48 hours post-treatment |
|---|---|
| 1 | 88 |
| 2 | 94 |
| 3 | 80 |
| 4 | 100 |
| 5 A | 10 |
| 5 B | 100 |
| 6 A | 81 |
| 6 B | 100 |
| 7 B | 100 |
| 9 | 100 |
| 10 A | 93 |
| 10 B | 100 |
| 11 | 90 |
| 12 | 75 |
| 13 | 95 |
| 17 | 6 |
| 18 | 22 |
| 22 | 100 |
| 25 | 100 |
| 26 | 100 |
| 27 | 94 |
| 28 | 100 |
| 29 | 100 |
| 30 | 100 |
| 31 | 64 |
| 32 | 100 |
| 34 | 16 |
| 35 | 46 |
| 36 A | 71 |
| 36 B | 82 |
| 37 A | 45 |
| 37 B | 100 |
| 38 | 100 |

| Compound | % Mortality 48 hours post-treatment |
|---|---|
| 40 | 96 |

The embodiments of the invention in which an exclusive property or privilege is claimed are defined as follows:

1. A phenoxypyridinyl compound of the formula

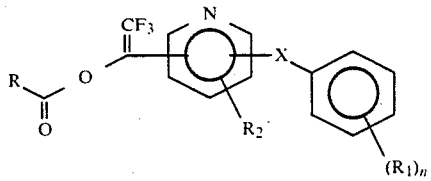

including all geometric and stereoisomers or mixtures thereof characterized by a 1,3-relationship between the ester and the ether substituents on the pyridine ring, wherein:

R is

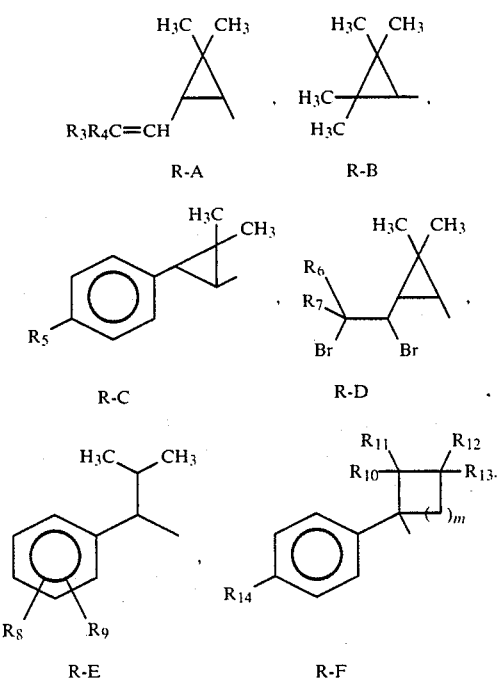

X is O or S;
n is 1 to 3;
m is 0 or 1;
$R_1$ is H, $C_1$ to $C_4$ alkyl, $C_2$ to $C_5$ alkenyl, $C_2$ to $C_5$ alkynyl, $C_1$ to $C_4$ haloalkyl, $C_1$ to $C_4$ alkoxy, $C_1$ to $C_4$ haloalkoxy, $C_1$ to $C_4$ alkylthio, $C_1$ to $C_4$ alkylsulfinyl, $C_1$ to $C_4$ alkylsulfonyl, $C_1$ to $C_4$ haloalkylthio, $C_1$ to $C_4$ haloalkylsulfonyl, F, Cl, Br; when n=2, the $R_1$ substituents, taken together, can be 3,4-methylenedioxy;
$R_2$ is H, F, Cl, Br, $CH_3$, or $CF_3$;
$R_3$ is F, Cl, Br, $C_1$ to $C_4$ alkyl, $C_1$ to $C_4$ haloalkyl, $CO_2CH_3$, or $CO_2CH_2CH_3$;
$R_4$ is F, Cl, Br, or $CH_3$;
$R_5$ is H, F, Cl, $CF_3$, or $C_1$ to $C_4$ alkyl;
$R_6$ is Cl or Br;
$R_7$ is Cl or Br;
$R_8$ is H, $C_1$ to $C_4$ alkyl, $C_1$ to $C_4$ haloalkyl, $C_1$ to $C_4$ alkoxy, $C_1$ to $C_4$ alkylthio, $C_1$ to $C_4$ alkylsulfinyl, $C_1$ to $C_4$ alkylsulfonyl, $C_1$ to $C_4$ haloalkylthio, $C_1$ to $C_4$ haloalkylsulfinyl, $C_1$ to $C_4$ haloalkylsulfonyl, F, Cl or Br;
$R_9$ is H, F, Cl, $CH_3$, $OCH_3$, or $R_8$ and $R_9$, taken together, can be 3,4-methylenedioxy;
$R_{10}$, $R_{11}$, $R_{12}$ and $R_{13}$ are independently H, F, or Cl; and
$R_{14}$ is H, F, Cl, $OCH_3$, $OCH_2CH_3$, or $C_1$ to $C_2$ haloalkoxy.

2. A compound according to claim 1 wherein the ester and ether substituents have the 1,3 relationship shown by the formula

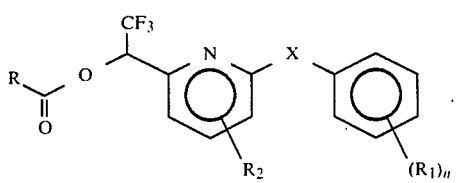

3. A compound according to claim 2 wherein:
X is O;
n is 1;
m is 1;
$R_1$ is H, $CH_3$, $CF_3$, $OCH_3$, $OCF_2H$, F, Cl, $SCH_3$, $SO_2CH_3$, $SCF_2H$, or $SO_2CF_2H$;
$R_2$ is H, F, or Cl;
$R_8$ is H, F, Cl, or $C_1$ to $C_2$ alkoxy;
$R_9$ is H; and
$R_{14}$ is H, F, Cl, $OCH_3$, $OCH_2CH_3$ or $OCF_2H$.

4. A compound according to claim 3 wherein R is selected from the group consisting of R-A, R-B, R-D and R-E.

5. A compound according to claim 4 wherein R is R-A.

6. A compound according to claim 5: [1-(6-phenoxy-2-pyridinyl)-2,2,2-trifluoroethyl]-3-(2-chloro-3,3,3-trifluoro-1-propenyl)-2,2-dimethylcyclopropanecarboxylate.

7. A compound according to claim 5: [1-(6-phenoxy-2-pyridinyl)-2,2,2-trifluoroethyl]-cis-(2,2-dichloroethenyl)-2,2-dimethylcyclopropanecarboxylate.

8. A compound according to claim 5: [1-(6-phenoxy-2-pyridinyl)-2,2,2-trifluoroethyl]-trans-3-(2,2-dichloroethenyl)-2,2-dimethylcyclopropanecarboxylate.

9. A compound according to claim 5: [1-(6-phenoxy-2-pyridinyl)-2,2,2-trifluoroethyl]-cis-3-(2,2-dibromoethenyl)-2,2-dimethylcyclopropanecarboxylate.

10. A compound according to claim 5: [1-(6-phenoxy-2-pyridinyl)-2,2,2-trifluoroethyl]-(1R)-cis-3-(2,2-dibromoethenyl)-2,2-dimethylcyclopropanecarboxylate.

11. A compound according to claim 5: [1-(6-phenoxy-2-pyridinyl)-(S)-2,2,2-trifluoroethyl]-(1R)-cis-3-(2,2-dibromoethenyl)-2,2-dimethylcyclopropanecarboxylate.

12. A compound according to claim 5: [1-(6-phenoxy-2-pyridinyl)-2,2,2-trifluoromethyl]-cis-3-(2-chloro-3,3,3-trifluoro-1-propenyl)-2,2-dimethylcyclopropanecarboxylate.

13. A stereoisomeric mixture according to claim 5: [1-(6-phenoxy-2-pyridinyl)-(R)-2,2,2-trifluoroethyl]-(1S)-cis-3-(2-chloro-3,3,3-trifluoro-1-propenyl)-2,2- dimethylcyclopropanecarboxylate and [1-(6-phenoxy-2-pyridinyl)-(S)-2,2,2-trifluoroethyl]-(1R)-cis-3-(2-chloro-3,3,3-trifluoro-1-propenyl)-2,2-dimethylcyclopropanecarboxylate.

14. A compound according to claim 5: [1-(6-phenoxy-2-pyridinyl)-(S)-2,2,2-trifluoroethyl]-(1R)-cis-3-(2-chloro-3,3,3-trifluoro-1-propenyl)-2,2-dimethylcyclopropanecarboxylate.

15. A compound according to claim 5: [1-[6-(4-fluorophenoxy)-2-pyridinyl]-2,2,2-trifluoroethyl]-cis-3-(2,2-dichloroethenyl)-2,2-dimethylcyclopropanecarboxylate.

16. A stereoisomeric mixture according to claim 5: [1-[6-(4-fluorophenoxy)-2-pyridinyl]-(R)-2,2,2-trifluoroethyl]-(1S)-cis-3-(2,2-dichloroethenyl)-2,2-dimethylcyclopropanecarboxylate and [1-[6-(4-fluorophenoxy)-2-pyridinyl]-(S)-2,2,2-trifluoroethyl]-(1R)-cis-3-(2,2-dichloroethenyl)-2,2-dimethylcyclopropanecarboxylate.

17. A compound according to claim 4 wherein R is R-B.

18. A compound according to claim 17: [1-[6-phenoxy-2-pyridinyl]-2,2,2-trifluoroethyl]-2,2,3,3-tetramethylcyclopropanecarboxylate.

19. A compound according to claim 17: [1-[6-(4-fluorophenoxy)-2-pyridinyl]-2,2,2-trifluoroethyl]2,2,3,3-tetramethylcyclopropanecarboxylate.

20. A compound according to claim 4 wherein R is R-D.

21. A compound according to claim 20: [1-[6-phenoxy-2-pyridinyl]-2,2,2-trifluoroethyl]-(1R)-cis-2,2-dimethyl-3-(1,2,2,2-tetrabromoethyl)cyclopropanecarboxylate.

22. A compound according to claim 4 wherein R is R-E.

23. A compound according to claim 22: [1-(6-phenoxy-2-pyridinyl)-2,2,2-trifluoroethyl]-4-chloro-α-(1-methylethyl)benzene acetate.

24. A compound of the formula

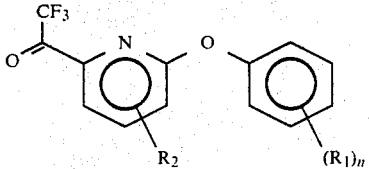

wherein:
R$_1$ is H, C$_1$ to C$_4$ alkyl, C$_2$ to C$_5$ alkenyl, C$_2$ to C$_5$ alkynyl, C$_1$ to C$_4$ haloalkyl, C$_1$ to C$_4$ alkoxy, C$_1$ to C$_4$ haloalkoxy, C$_1$ to C$_4$ alkylthio, C$_1$ to C$_4$ alkylsulfinyl, C$_1$ to C$_4$ alkylsulfonyl, C$_1$ to C$_4$ haloalkylthio, C$_1$ to C$_4$ haloalkylsulfonyl, F, Cl, Br; when n=2, the R$_1$ substituents, taken together, can be 3,4-methylenedioxy;
R$_2$ is H, F, Cl, Br, CH$_3$ or CF$_3$; and
n is 1 to 3.

25. A compound according to claim 24: 1-(6-phenoxy-2-pyridinyl)-2,2,2-trifluoroethanone.

26. A compound of the formula

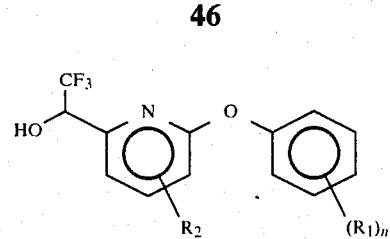

wherein:
R$_1$ is H, C$_1$ to C$_4$ alkyl, C$_2$ to C$_5$ alkenyl, C$_2$ to C$_5$ alkynyl, C$_1$ to C$_4$ haloalkyl, C$_1$ to C$_4$ alkoxy, C$_1$ to C$_4$ haloalkoxy, C$_1$ to C$_4$ alkylthio, C$_1$ to C$_4$ alkylsulfinyl, C$_1$ to C$_4$ alkylsulfonyl, C$_1$ to C$_4$ haloalkylthio, C$_1$ to C$_4$ haloalkylsulfonyl, F, Cl, Br; when n=2, the R$_1$ substituents, taken together, can be 3,4-methylenedioxy;
R$_2$ is H, F, Cl, Br, CH$_3$, or CF$_3$; and
n is 1 to 3.

27. A compound according to claim 26: 1-(6-phenoxy-2-pyridinyl)-2,2,2-trifluoroethanol.

28. A compound according to claim 26: 1-(6-phenoxy-2-pyridinyl)-(S)-2,2,2-trifluoroethanol.

29. A method for making a compound according to claim 24 comprising:
(i) metallating the following phenoxy or thiophenoxy pyridinyl halide,

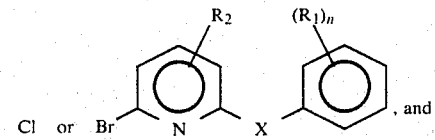

(ii) reacting the metallated product of step (i) with N,N-dimethyltrifluoroacetamide (CF$_3$CON(CH$_3$)$_2$) to form the corresponding phenoxypyridinyltrifluoroethanone wherein: R$_1$, R$_2$, X and n are as previously defined.

30. A method for making a compound according to claim 26 comprising:
(i) metallating the following phenoxy or thiophenoxy pyridinyl halide,

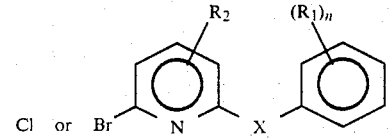

(ii) reacting the metallated product of step (i) with N,N-dimethyltrifluoroacetamide (CF$_3$CON(CH$_3$)$_2$) to form the corresponding phenoxypyridinyltrifluoroethanone wherein: R$_1$, R$_2$, X and n are as previously defined, and
(iii) reducing the ketone of step (ii).

31. An insecticidal and acaricidal composition comprising a compound according to claim 1 and an agriculturally suitable diluent or carrier.

32. An insecticidal and acaricidal composition comprising a compound according to claim 2 and an agriculturally suitable diluent or carrier.

33. An insecticidal and acaricidal composition comprising a compound according to claim 3 and an agriculturally suitable diluent or carrier.

34. An insecticidal and acaricidal composition comprising a compound according to claim 4 and an agriculturally suitable diluent or carrier.

35. An insecticidal and acaricidal composition comprising a compound according to claim 5 and an agriculturally suitable diluent or carrier.

36. An insecticidal and acaricidal composition comprising a compound according to claim 17 and an agriculturally suitable diluent or carrier.

37. An insecticidal and acaricidal composition comprising a compound according to claim 20 and an agriculturally suitable diluent or carrier.

38. An insecticidal and acaricidal composition comprising a compound according to claim 22 and an agriculturally suitable diluent or carrier.

39. An insecticidal and acaricidal composition comprising a first component of a compound according to claim 1 and a second component selected from at least one other agriculturally effective compound in a diluent or carrier.

40. A method for controlling acarides or insects that comprises applying to the pest or to the environment of the acaride or insect an insecticidally and acaricidally effective amount of a compound according to claim 1.

41. A method for controlling acarides or insects that comprises applying to the pest or to the environment of the acaride or insect an insecticidally and acaricidally effective amount of a compound according to claim 2.

42. A method for controlling acarides or insects that comprises applying to the pest or to the environment of the acaride or insect an insecticidally and acaricidally effective amount of a compound according to claim 3.

43. A method for controlling acarides or insects that comprises applying to the pest or to the environment of the acaride or Insect an insecticidally and acaricidally amount of a compound according to claim 4.

44. A method for controlling acarides or insects that comprises applying to the pest or to the environment of the acaride or insect an insecticidally and acaricidally effective amount of a compound according to claim 5.

45. A method for controlling acarides or insects that comprises applying to the pest or to the environment of the acaride or insect an insecticidally and acaricidally effective amount of a compound according to claim 17.

46. A method for controlling acarides or insects that comprises applying to the pest or to the environment of the acaride or insect an insecticidally and acaricidally effective amount of a compound according to claim 20.

47. A method for controlling acarides or insects that comprises applying to the pest or to the environment of the acaride or insect an insecticidally and acaricidally effective amount of a compound according to claim 22.

48. A method for controlling acarides or insects that comprises applying to the pest or to the environment of the acaride or insect an insecticidally and acaricidally effective amount of a composition according to claim 31.

49. A method for controlling acarides or insects that comprises applying to the pest or to the environment of the acaride or insect an insecticidally and acaricidally effective amount of a composition according to claim 39.

50. A compound according to claim 5 wherein $R_1$ is H, $R_2$ is 5-H and $R_3$ and $R_4$ are each Cl.

51. An insecticidal and acaricidal composition comprising a compound according to claim 50 and an agriculturally suitable diluent or carrier.

52. A method for controlling acarides or insects that comprises applying to the acaride or insect or to the environment of the pest an insecticidally and acaricidally effective amount of a compound according to claim 50.

53. A method for controlling acarides or insects that comprises applying to the acaride or insect or to the environment of the pest an insectically and acaricidally effective amount of a composition according to claim 51.

* * * * *

UNITED STATES PATENT AND TRADEMARK OFFICE
CERTIFICATE OF CORRECTION

PATENT NO. : 4,694,013

DATED : September 15, 1987

INVENTOR(S) : George Philip Lahm

It is certified that error appears in the above-identified patent and that said Letters Patent is hereby corrected as shown below:

The spelling of "Phenoxypyridinyl" should be corrected in the Title of the patent on page 1 and at the top of column 1.

<u>In the Specification</u>:

At column 4, line 45, the structure should appear as follows:

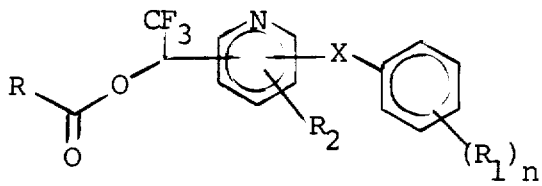

<u>In the Claims</u>:

In Claim 1, column 43, line 15, the structure should appear as follows:

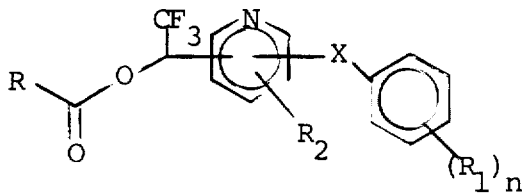

UNITED STATES PATENT AND TRADEMARK OFFICE
CERTIFICATE OF CORRECTION

PATENT NO. : 4,694,013
DATED : September 15, 1987
INVENTOR(S) : George Philip Lahm It is certified that error appears in the above-identified patent and that said Letters Patent is hereby corrected as shown below:

In Claim 7, column 44, line 46, "3-" should appear after "-cis-".
In Claim 50, column 48, line 26, "5-H" should be --5-F--.

Signed and Sealed this

Thirty-first Day of May, 1988

Attest:

DONALD J. QUIGG

Attesting Officer

Commissioner of Patents and Trademarks